(12) United States Patent
Angell et al.

(10) Patent No.: US 8,145,582 B2
(45) Date of Patent: Mar. 27, 2012

(54) SYNTHETIC EVENTS FOR REAL TIME PATIENT ANALYSIS

(75) Inventors: Robert L. Angell, Salt Lake City, UT (US); Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 900 days.

(21) Appl. No.: 12/135,972

(22) Filed: Jun. 9, 2008

(65) Prior Publication Data

US 2008/0294692 A1 Nov. 27, 2008

Related U.S. Application Data

(63) Continuation-in-part of application No. 12/121,947, filed on May 16, 2008, and a continuation-in-part of application No. 11/678,959, filed on Feb. 26, 2007, now Pat. No. 7,752,154, and a continuation-in-part of application No. 11/542,397, filed on Oct. 3, 2006, now Pat. No. 7,809,660.

(51) Int. Cl.
*G06F 17/00* (2006.01)
*G06N 5/00* (2006.01)
(52) U.S. Cl. .......................................... 706/45
(58) Field of Classification Search .................. None
See application file for complete search history.

(56) References Cited

U.S. PATENT DOCUMENTS

| | | | |
|---|---|---|---|
| 4,328,978 A | 5/1982 | McLaughlin |
| 4,551,842 A | 11/1985 | Segarra |
| 4,841,526 A | 6/1989 | Wilson et al. |
| 4,890,227 A | 12/1989 | Watanabe et al. |
| 5,070,453 A | 12/1991 | Duffany |
| 5,128,871 A | 7/1992 | Schmitz |
| 5,237,429 A | 8/1993 | Zuiss et al. |

(Continued)

FOREIGN PATENT DOCUMENTS

EP  0772367  5/1997

(Continued)

OTHER PUBLICATIONS

Xing et al. "Bayesian Multi-Population Haplotype Inference via a Hierarchical Dirichlet Process Mixture", ICDM, 2006, pp. 8.*

(Continued)

*Primary Examiner* — Jeffrey A Gaffin
*Assistant Examiner* — Li-Wu Chang
(74) *Attorney, Agent, or Firm* — Yee & Associates, P.C.; John R. Pivnichny

(57) ABSTRACT

Generating synthetic events based on a vast amount of data. First and second data are received. The first data is organized into a first cohort. The second data is organized into a second cohort. The first cohort and the second cohort are processed to generate a synthetic event. The synthetic event comprises third data representing a result of a mathematical computation defined by $S(p1) \Longrightarrow F(p2)$, wherein S comprises input facts with probability $p1$, wherein the input facts comprise the first cohort and the second cohort, and wherein F comprises an inferred event with probability $p2$. The term "event" means a particular set of data that represents, encodes, or records at least one of a thing or happening. Each of the first data, the second data, the first cohort, the second cohort, the synthetic event, and subcomponents thereof all comprise different events. The synthetic event is stored.

15 Claims, 16 Drawing Sheets

U.S. PATENT DOCUMENTS

| | | | |
|---|---|---|---|
| 5,406,626 A | 4/1995 | Ryan | |
| 5,455,868 A | 10/1995 | Sergent et al. | |
| 5,524,051 A | 6/1996 | Ryan | |
| 5,550,021 A | 8/1996 | Blum et al. | |
| 5,491,838 A | 11/1996 | Takahisa | |
| 5,577,266 A | 11/1996 | Takahisa et al. | |
| 5,590,195 A | 12/1996 | Ryan | |
| 5,613,194 A | 3/1997 | Olds et al. | |
| 5,642,397 A | 6/1997 | Agbaje-Anozie | |
| 5,659,596 A | 8/1997 | Dunn | |
| 5,692,446 A | 12/1997 | Becker et al. | |
| 5,692,501 A | 12/1997 | Minturn | |
| 5,745,532 A | 4/1998 | Campana, Jr. | |
| 5,751,806 A | 5/1998 | Ryan | |
| 5,764,740 A | 6/1998 | Holender | |
| 5,781,704 A | 7/1998 | Rossmo | |
| 5,809,472 A | 9/1998 | Morrison | |
| 5,815,971 A | 10/1998 | Rothe et al. | |
| 5,825,755 A | 10/1998 | Thompson et al. | |
| 5,838,918 A | 11/1998 | Prager et al. | |
| 5,880,598 A | 3/1999 | Duong | |
| 5,889,474 A | 3/1999 | LaDue | |
| 5,926,624 A | 7/1999 | Katz et al. | |
| 5,930,350 A | 7/1999 | Johnson | |
| 5,965,352 A | 10/1999 | Stoughton et al. | |
| 5,974,312 A | 10/1999 | Hayes, Jr. et al. | |
| 5,982,281 A | 11/1999 | Layson, Jr. | |
| 5,993,386 A | 11/1999 | Ericsson | |
| 6,021,403 A | 2/2000 | Horvitz et al. | |
| 6,058,391 A | 5/2000 | Gardner | |
| 6,076,166 A | 6/2000 | Moshfeghi et al. | |
| 6,167,405 A | 12/2000 | Rosensteel, Jr. et al. | |
| 6,189,004 B1 | 2/2001 | Rassen et al. | |
| 6,192,340 B1 | 2/2001 | Abecassis | |
| 6,212,524 B1 | 4/2001 | Weissman et al. | |
| 6,216,134 B1 | 4/2001 | Heckerman et al. | |
| 6,269,365 B1 | 7/2001 | Kiyoki et al. | |
| 6,278,999 B1 | 8/2001 | Knapp | |
| 6,285,886 B1 | 9/2001 | Kamel et al. | |
| 6,321,207 B1 | 11/2001 | Ye | |
| 6,353,818 B1 | 3/2002 | Carino, Jr. | |
| 6,370,931 B2 | 4/2002 | Bennett | |
| 6,377,993 B1 | 4/2002 | Brandt et al. | |
| 6,385,604 B1 | 5/2002 | Bakalash et al. | |
| 6,484,155 B1 | 11/2002 | Kiss et al. | |
| 6,506,384 B1 | 1/2003 | Laal et al. | |
| 6,509,898 B2 | 1/2003 | Chi et al. | |
| 6,563,804 B1 | 5/2003 | Iyer et al. | |
| 6,578,043 B2 | 6/2003 | Nye | |
| 6,581,037 B1 | 6/2003 | Pak | |
| 6,606,625 B1 | 8/2003 | Muslea et al. | |
| 6,629,106 B1 | 9/2003 | Narayanaswamy et al. | |
| 6,662,141 B2 | 12/2003 | Kaub | |
| 6,675,159 B1 | 1/2004 | Lin et al. | |
| 6,714,979 B1 | 3/2004 | Brandt et al. | |
| 6,823,818 B2 | 11/2004 | van den Berg et al. | |
| 6,826,568 B2 | 11/2004 | Bernstein et al. | |
| 6,829,604 B1 | 12/2004 | Tifft | |
| 6,905,816 B2 | 6/2005 | Jacobs et al. | |
| 6,937,147 B2 | 8/2005 | Dilbeck et al. | |
| 6,941,311 B2 | 9/2005 | Shah et al. | |
| 6,954,736 B2 | 10/2005 | Menninger et al. | |
| 6,963,826 B2 | 11/2005 | Hanaman et al. | |
| 6,965,816 B2 | 11/2005 | Walker | |
| 6,972,687 B1 | 12/2005 | Marshall et al. | |
| 6,978,268 B2 | 12/2005 | Thomas et al. | |
| 6,996,567 B2 | 2/2006 | Ghukasyan | |
| 7,019,740 B2 | 3/2006 | Georgalas | |
| 7,047,253 B1 | 5/2006 | Murthy et al. | |
| 7,072,794 B2 | 7/2006 | Wittkowski | |
| 7,080,081 B2 | 7/2006 | Agarwal et al. | |
| 7,089,250 B2 | 8/2006 | Doganata et al. | |
| 7,111,010 B2 | 9/2006 | Chen | |
| 7,152,070 B1 | 12/2006 | Musick et al. | |
| 7,179,645 B2 | 2/2007 | Humphreys et al. | |
| 7,181,428 B2 | 2/2007 | Lawrence | |
| 7,191,183 B1 | 3/2007 | Goldstein | |
| 7,213,009 B2 | 5/2007 | Pestotnik et al. | |
| 7,230,930 B2 | 6/2007 | Ahya et al. | |
| 7,240,330 B2 | 7/2007 | Fairweather | |
| 7,295,925 B2 | 11/2007 | Breed et al. | |
| 7,346,492 B2 | 3/2008 | Shaw | |
| 7,403,922 B1 | 7/2008 | Lewis et al. | |
| 7,433,853 B2 | 10/2008 | Brockway et al. | |
| 7,457,810 B2 | 11/2008 | Breining et al. | |
| 7,500,150 B2 | 3/2009 | Sharma et al. | |
| 7,533,113 B1 | 5/2009 | Haddad | |
| 7,543,149 B2 | 6/2009 | Ricciardi et al. | |
| 7,580,922 B2 | 8/2009 | Friedlander et al. | |
| 7,630,330 B2 | 12/2009 | Gatts | |
| 7,631,222 B2 | 12/2009 | Hasan et al. | |
| 7,644,056 B2 | 1/2010 | Khalsa | |
| 7,676,390 B2 | 3/2010 | Senturk et al. | |
| 7,685,083 B2 | 3/2010 | Fairweather | |
| 2001/0051881 A1 | 12/2001 | Filler | |
| 2002/0004725 A1 | 1/2002 | Martin et al. | |
| 2002/0004782 A1 | 1/2002 | Cincotta | |
| 2002/0049772 A1 | 4/2002 | Rienhoff, Jr. et al. | |
| 2002/0052756 A1 | 5/2002 | Lomangino | |
| 2002/0082806 A1 | 6/2002 | Kaub | |
| 2002/0099691 A1 | 7/2002 | Lore et al. | |
| 2002/0107824 A1 | 8/2002 | Ahmed | |
| 2002/0111922 A1 | 8/2002 | Young et al. | |
| 2002/0150957 A1 | 10/2002 | Slotman | |
| 2002/0156791 A1 | 10/2002 | Nesamoney et al. | |
| 2002/0184401 A1 | 12/2002 | Kadel, Jr. et al. | |
| 2003/0014400 A1 | 1/2003 | Siegel | |
| 2003/0033263 A1 | 2/2003 | Cleary | |
| 2003/0037063 A1 | 2/2003 | Schwartz | |
| 2003/0074222 A1 | 4/2003 | Rosow et al. | |
| 2003/0088365 A1 | 5/2003 | Becker | |
| 2003/0088438 A1 | 5/2003 | Maughan et al. | |
| 2003/0093187 A1 | 5/2003 | Walker | |
| 2003/0120651 A1 | 6/2003 | Bernstein et al. | |
| 2003/0126148 A1 | 7/2003 | Gropper et al. | |
| 2003/0140063 A1 | 7/2003 | Pizzorno et al. | |
| 2003/0171876 A1 | 9/2003 | Markowitz et al. | |
| 2003/0177038 A1 | 9/2003 | Rao | |
| 2003/0191699 A1 | 10/2003 | Deveauet et al. | |
| 2003/0200531 A1 | 10/2003 | Fairweather | |
| 2003/0212546 A1 | 11/2003 | Shaw | |
| 2004/0006532 A1 | 1/2004 | Lawrence et al. | |
| 2004/0006694 A1 | 1/2004 | Heelan et al. | |
| 2004/0054144 A1 | 3/2004 | Itai | |
| 2004/0122787 A1 | 6/2004 | Avinash et al. | |
| 2004/0193572 A1 | 9/2004 | Leary | |
| 2004/0249678 A1 | 12/2004 | Henderson | |
| 2004/0249679 A1 | 12/2004 | Henderson et al. | |
| 2005/0004823 A1 | 1/2005 | Hnatio | |
| 2005/0038608 A1 | 2/2005 | Chandra et al. | |
| 2005/0049988 A1 | 3/2005 | Dahlquist et al. | |
| 2005/0050068 A1 | 3/2005 | Vaschillo et al. | |
| 2005/0055257 A1 | 3/2005 | Senturk et al. | |
| 2005/0080806 A1 | 4/2005 | Doganata et al. | |
| 2005/0102210 A1 | 5/2005 | Song et al. | |
| 2005/0144062 A1 | 6/2005 | Mittal et al. | |
| 2005/0149466 A1 | 7/2005 | Hale et al. | |
| 2005/0165594 A1 | 7/2005 | Chandra et al. | |
| 2005/0246189 A1 | 11/2005 | Monitzer et al. | |
| 2006/0010090 A1 | 1/2006 | Brockway et al. | |
| 2006/0036560 A1 | 2/2006 | Fogel | |
| 2006/0041659 A1 | 2/2006 | Hasan et al. | |
| 2006/0069514 A1 | 3/2006 | Chow et al. | |
| 2006/0155627 A1 | 7/2006 | Horowitz | |
| 2006/0184483 A1 | 8/2006 | Clark et al. | |
| 2006/0200435 A1 | 9/2006 | Flinn et al. | |
| 2006/0218010 A1 | 9/2006 | Michon et al. | |
| 2006/0282222 A1 | 12/2006 | Mitsuyama et al. | |
| 2006/0287890 A1 | 12/2006 | Stead et al. | |
| 2007/0027674 A1 | 2/2007 | Parson et al. | |
| 2007/0073654 A1 | 3/2007 | Chow et al. | |
| 2007/0073754 A1 | 3/2007 | Friedlander et al. | |
| 2007/0106478 A1 | 5/2007 | Jung et al. | |
| 2007/0112714 A1 | 5/2007 | Fairweather | |
| 2007/0174090 A1 | 7/2007 | Friedlander et al. | |
| 2007/0174091 A1 | 7/2007 | Friedlander et al. | |
| 2007/0185586 A1 | 8/2007 | Al-Attar et al. | |

| | | |
|---|---|---|
| 2007/0185737 A1 | 8/2007 | Friedlander et al. |
| 2007/0198450 A1 | 8/2007 | Khalsa |
| 2007/0198518 A1* | 8/2007 | Luchangco et al. ............... 707/8 |
| 2007/0203872 A1 | 8/2007 | Flinn et al. |
| 2007/0233631 A1 | 10/2007 | Kobayashi et al. |
| 2007/0244701 A1 | 10/2007 | Erlanger et al. |
| 2007/0274337 A1 | 11/2007 | Purpura |
| 2007/0276851 A1 | 11/2007 | Friedlander et al. |
| 2007/0299691 A1 | 12/2007 | Friedlander et al. |
| 2008/0015871 A1 | 1/2008 | Eder |
| 2008/0065576 A1 | 3/2008 | Friedlander et al. |
| 2008/0077463 A1 | 3/2008 | Friedlander et al. |
| 2008/0082356 A1 | 4/2008 | Friedlander et al. |
| 2008/0082374 A1 | 4/2008 | Kennis et al. |
| 2008/0114779 A1 | 5/2008 | Friedlander et al. |
| 2008/0172352 A1 | 7/2008 | Friedlander et al. |
| 2008/0177687 A1 | 7/2008 | Friedlander et al. |
| 2008/0177688 A1 | 7/2008 | Friedlander et al. |
| 2008/0208801 A1 | 8/2008 | Friedlander et al. |
| 2008/0208813 A1 | 8/2008 | Friedlander et al. |
| 2008/0208814 A1 | 8/2008 | Friedlander et al. |
| 2008/0208832 A1 | 8/2008 | Friedlander et al. |
| 2008/0208838 A1 | 8/2008 | Friedlander et al. |
| 2008/0208875 A1 | 8/2008 | Friedlander et al. |
| 2008/0208902 A1 | 8/2008 | Friedlander et al. |
| 2008/0208903 A1 | 8/2008 | Friedlander et al. |
| 2008/0208904 A1 | 8/2008 | Friedlander et al. |
| 2008/0228747 A1 | 9/2008 | Thrall et al. |
| 2008/0294692 A1 | 11/2008 | Angell et al. |

FOREIGN PATENT DOCUMENTS

| | | |
|---|---|---|
| EP | 0959635 | 11/1999 |
| JP | 8316872 | 11/1996 |
| JP | 2002312373 | 4/2001 |
| JP | 2002342484 | 2/2002 |
| WO | 9419571 | 9/1994 |
| WO | 9726718 | 7/1997 |
| WO | 0108077 | 2/2001 |

OTHER PUBLICATIONS

Tracy et al. "An Agent-based Approach to Inference Prevention in Distributed Database Systems", ICTAI, 2002, pp. 10.*
Luckham et al., Event Processing Glossary, pp. 1-13 http://complexevents.com/?p=361 retrieved Jun. 9, 2008.
U.S. Appl. No. 11/678,959, filed Feb. 26, 2007, Friedlander et al.
U.S. Appl. No. 12/135,960, filed Jun. 9, 2008, Angell et al.
U.S. Appl. No. 11/516,954, filed Sep. 7, 2006, Friedlander et al.
U.S. Appl. No. 11/874,382, filed Oct. 18, 2007, Friedlander et al.
U.S. Appl. No. 12/130,779, filed May 30, 2008, Friedlander et al.
U.S. Appl. No. 12/121,947, filed May 16, 2008, Angell et al.
U.S. Appl. No. 12/243,825, filed Oct. 1, 2008, Angell et al.
"AHRQ Quality Indicators—Patient Safety Indicators—Technical Specifications", Department of Health and Human Services Agency for Healthcare Research and Quality, Version 3.1, Mar. 12, 2007, pp. 1-107, <http://www.qualityindicators.ahrq.gov>.
Hayes et al., "Picking Up the Pieces: Utilizing Disaster Recovery Project Management to Improve Readiness and Response Time", IEEE Industry Applications Magazine, Nov./Dec. 2002, pp. 1-10.
Wang et al., "A Mathematical Approach to Disaster Recovery Planning", Xidian University, National Info Security Engineering and Technology Research Center, Beijing, China, Proceedings of the First International Conference of Semantics, Knowledge, and Grid, SKG 2005, pp. 1-3.
Silver, E.A., "An Overview of Heuristic Solution Methods", The Journal of the Operational Research Society, vol. 55, No. 9, Sep. 2004, pp. 936-956.
Chen et al., "Research on Organization Method of Development Activities for Complicated Product", The 9th International Conference on Computer Supported Cooperative Work in Design Proceedings, vol. 1, May 24-26, 2005, pp. 234-239.
Cao et al., "Research on Resource Scheduling for Development Process of Complicated Product", The 9th International Conference on Computer Supported Cooperative Work in Design Proceedings, vol. 1, May 24-26, 2005, pp. 229-331.

Altmann et al., "Cooperative Software Development: Concepts, Model and Tools", C Doppler Laboratory for Software Engineering, Johannes Kepler University, Linz, 1999, pp. 194-207.
Souder, William E., "Analytical Effectiveness of Mathematical Models for R&D Project Selection", Management Science, Application Series, vol. 19, No. 8, Apr. 1973, pp. 907-923.
Beaglehole, R, Men Ageing and Health: Achieving health across the life span, 2nd World Congress on the Ageing Male, World Health Organization, Feb. 2000, pp. 1-63.
Goehring, "Identification of Patients in Medical Databases—Soundex Codes Versus Match Code", Medical Informatics, vol. 10, No. 1, pp. 27-34, Jan.-Mar. 1985, Abstract Only.
Goodwin et al., "Data Mining for Preterm Birth Prediction", pp. 46-51.
Grimson et al., "The SI Challenge in Health Care", Communications of the ACM, vol. 43, No. 6, Jun. 2000, pp. 49-55.
Han and Fu, "Discovery of Multiple-Level Association Rules from Large Databases," In: Proceedings of the 21st VLDB Conference (1995). http://citeseerx.ist.psu.edu/viewdoc/download?doi=10.1.1.64.3214&rep1&type=pdf.
Hashemi et al., "Development of Group's Signature for Evaluation of Skin Cancer in Mice Cause by Ultraviolet Radiation", Proceedings of the International Conference of Information Technology: Computers and Communications, ITCC 2003, IEEE Computer Society, Washington, DC, USA, Apr. 28-30, 2003, pp. 1-4.
Hoshiai et al., "SION Architecture: Semantic Information-Oriented Network Architecture", Transactions of the Institute of Electronics, Information and Communication Engineers, vol. J84-B, No. 3, pp. 411-424, Mar. 2001, Abstract Only.
Johansson et al., "Visual Analysis Based on Algorithmic Classification", Proceedings of the Seventh International Conference on Information Visualization, London, England, Jul. 16-18, 2003, pp. 1-4.
Karlaftis et al., "Effects of road geometry and traffic volumes on rural roadway accident rates" Accident Analysis and Prevention 34, 357-365 2002.
Kiang, "Extending the Kohonen Self-Organizing Map Networks for Clustering Analysis", Journal, Computational Statistics & Data Analysis, vol. 38, Dec. 2, 2001, pp. 161-180.
Lowery et al., "Barriers to Implementing Simulation in Health Care", Proceedings from the 1994 Winter Simulation Conference, pp. 868-875.
Shelfer et al., "Smart Card Evolution", Communications of the ACM, vol. 45, No. 7, Jul. 2002, pp. 83-88, Abstract Only.
USPTO office action for U.S. Appl. No. 11/516,954 dated Dec. 19, 2008.
USPTO notice of allowance for U.S. Appl. No. 11/516,954 dated Jul. 16, 2009.
USPTO office action for U.S. Appl. No. 11/678,959 dated Feb. 19, 2009.
USPTO final office action for U.S. Appl. No. 11/678,959 dated Aug. 10, 2009.
USPTO notice of allowance for U.S. Appl. No. 11/678,959 dated Feb. 24, 2010.
USPTO office action for U.S. Appl. No. 11/734,079 dated May 14, 2009.
USPTO final office action for U.S. Appl. No. 11/734,079 dated Sep. 28, 2009.
USPTO notice of allowance for U.S. Appl. No. 11/734,079 dated Dec. 2, 2009.
USPTO office action for U.S. Appl. No. 11/734,098 dated Mar. 2, 2010.
USPTO office action for U.S. Appl. No. 11/741,538 dated Jul. 22, 2009.
USPTO notice of allowance for U.S. Appl. No. 11/741,538 dated Dec. 22, 2009.
USPTO notice of allowance for U.S. Appl. No. 11/741,538 dated Jul. 22, 2009.
USPTO office action for U.S. Appl. No. 11/741,467 dated Aug. 6, 2009.
USPTO final office action for U.S. Appl. No. 11/741,467 dated Dec. 21, 2009.
USPTO office action for U.S. Appl. No. 11/542,397 dated Dec. 30, 2009.

USPTO notice of allowance for U.S. Appl. No. 11/542,397 dated May 26, 2010.
USPTO office action for U.S. Appl. No. 11/678,997 dated Apr. 15, 2009.
USPTO final office action for U.S. Appl. No. 11/678,997 dated Oct. 5, 2009.
USPTO notice of allowance for U.S. Appl. No. 11/678,997 dated Apr. 6, 2010.
USPTO final office action for U.S. Appl. No. 11/678,997 dated Sep. 15, 2009.
USPTO office action for U.S. Appl. No. 11/678,997 dated Dec. 21, 2010.
USPTO office action for U.S. Appl. No. 11/678,997 dated Apr. 21, 2010.
USPTO office action for U.S. Appl. No. 11/678,957 dated Nov. 27, 2009.
USPTO final office action for U.S. Appl. No. 11/678,957 dated May 12, 2010.
USPTO office action for U.S. Appl. No. 11/678,976 dated Apr. 15, 2009.
USPTO final office action for U.S. Appl. No. 11/678,976 dated Sep. 14, 2009.
USPTO office action for U.S. Appl. No. 11/678,976 dated Dec. 21, 2009.
USPTO notice of allowance for U.S. Appl. No. 11/678,976 dated Apr. 21, 2010.
USPTO office action for U.S. Appl. No. 11/679,009 dated Apr. 15, 2009.
USPTO final office action for U.S. Appl. No. 11/679,009 dated Sep. 15, 2009.
USPTO office action for U.S. Appl. No. 11/679,009 dated Dec. 21, 2009.
USPTO notice of allowance for U.S. Appl. No. 11/679,009 dated May 19, 2010.
USPTO notice of allowance for U.S. Appl. No. 11/968,233 dated Mar. 24, 2010.
USPTO office action for U.S. Appl. No. 11/864,050 dated Jan. 9, 2009.
USPTO final office action for U.S. Appl. No. 11/864,050 dated Apr. 30, 2009.
USPTO notice of allowance action for U.S. Appl. No. 11/864,050 dated Aug. 31, 2009.
USPTO office action for U.S. Appl. No. 11/863,992 dated Dec. 22, 2008.
USPTO final office action for U.S. Appl. No. 11/863,992 dated Apr. 30, 2009.
USPTO notice of allowance for U.S. Appl. No. 11/863,992 dated Sep. 8, 2009.
USPTO office action for U.S. Appl. No. 11/864,039 dated Jan. 2, 2009.
USPTO final office action for U.S. Appl. No. 11/864,039 dated Apr. 30, 2009.
USPTO notice of allowance for U.S. Appl. No. 11/864,039 dated Sep. 1, 2009.
USPTO office action for U.S. Appl. No. 11/864,002 dated Dec. 22, 2008.
USPTO final office action for U.S. Appl. No. 11/864,002 dated Apr. 17, 2009.
USPTO notice of allowance for U.S. Appl. No. 11/864,002 dated Sep. 11, 2009.
USPTO office action for U.S. Appl. No. 12/130,814 dated Feb. 5, 2010.
USPTO notice of allowance for U.S. Appl. No. 12/130,814 dated Apr. 28, 2010.
USPTO office action for U.S. Appl. No. 12/130,543 dated Feb. 3, 2010.
USPTO notice of allowance for U.S. Appl. No. 12/130,543 dated May 25, 2010.
USPTO office action for U.S. Appl. No. 12/121,947 dated Jun. 12, 2010.

* cited by examiner

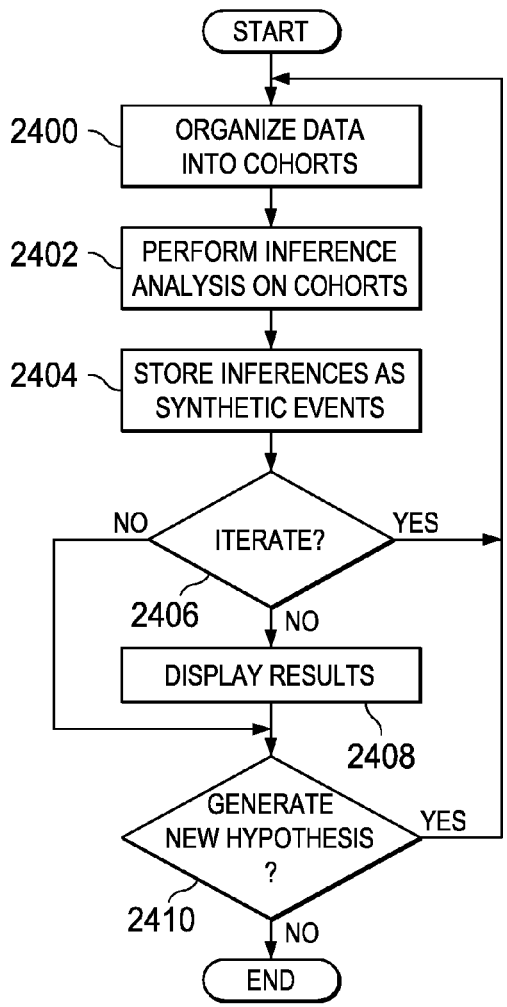
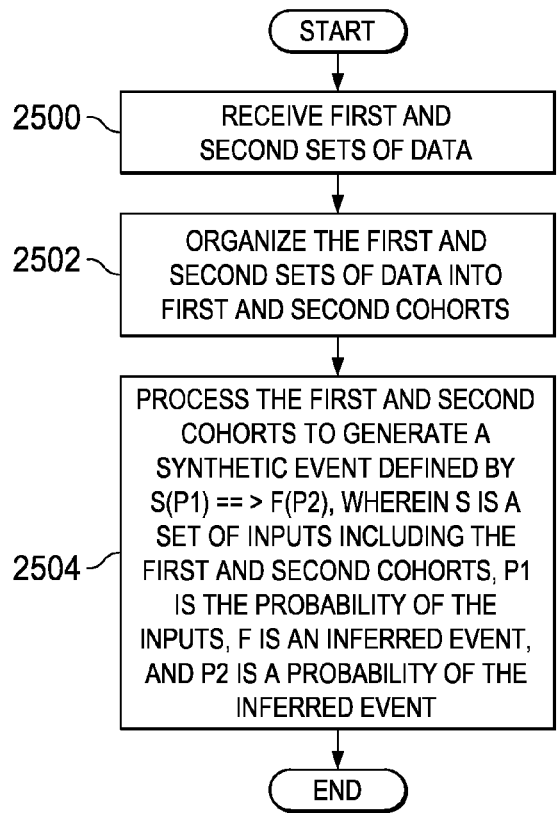

SYNTHETIC EVENTS FOR REAL TIME PATIENT ANALYSIS

This application is a continuation-in-part of the following: U.S. application Ser. No. 12/121,947, "Analysis of Individual and Group Healthcare Data in order To Provide Real Time Healthcare Recommendations," filed May 16, 2008; U.S. application Ser. No. 11/678,959, "System and Method for Deriving a Hierarchical Event Based Database Optimized for Analysis of Criminal and Security Information," filed Feb. 26, 2007; and U.S. Application Ser. No. 11,542,397, "System and Method To Optimize Control Cohorts Using Clustering Algorithms," filed Oct. 3, 2006.

BACKGROUND OF THE INVENTION

1. Field of the Invention

The present invention relates generally to selecting control cohorts and more particularly, to a computer implemented method, apparatus, and computer usable program code for automatically selecting a control cohort or for analyzing individual and group healthcare data in order to provide real time healthcare recommendations.

2. Description of the Related Art

A cohort is a group of individuals, machines, components, or modules identified by a set of one or more common characteristics. This group is studied over a period of time as part of a scientific study. A cohort may be studied for medical treatment, engineering, manufacturing, or for any other scientific purpose. A treatment cohort is a cohort selected for a particular action or treatment.

A control cohort is a group selected from a population that is used as the control. The control cohort is observed under ordinary conditions while another group is subjected to the treatment or other factor being studied. The data from the control group is the baseline against which all other experimental results must be measured. For example, a control cohort in a study of medicines for colon cancer may include individuals selected for specified characteristics, such as gender, age, physical condition, or disease state that do not receive the treatment.

The control cohort is used for statistical and analytical purposes. Particularly, the control cohorts are compared with action or treatment cohorts to note differences, developments, reactions, and other specified conditions. Control cohorts are heavily scrutinized by researchers, reviewers, and others that may want to validate or invalidate the viability of a test, treatment, or other research. If a control cohort is not selected according to scientifically accepted principles, an entire research project or study may be considered of no validity wasting large amounts of time and money. In the case of medical research, selection of a less than optimal control cohort may prevent proving the efficacy of a drug or treatment or incorrectly rejecting the efficacy of a drug or treatment. In the first case, billions of dollars of potential revenue may be lost. In the second case, a drug or treatment may be necessarily withdrawn from marketing when it is discovered that the drug or treatment is ineffective or harmful leading to losses in drug development, marketing, and even possible law suits.

Control cohorts are typically manually selected by researchers. Manually selecting a control cohort may be difficult for various reasons. For example, a user selecting the control cohort may introduce bias. Justifying the reasons, attributes, judgment calls, and weighting schemes for selecting the control cohort may be very difficult. Unfortunately, in many cases, the results of difficult and prolonged scientific research and studies may be considered unreliable or unacceptable requiring that the results be ignored or repeated. As a result, manual selection of control cohorts is extremely difficult, expensive, and unreliable.

An additional problem facing those in the art of data management is computationally explosive tasks. A computer process, a comparison of data, or some other computer-implemented analysis is considered computationally explosive when the number of possible permutations in the analysis is sufficiently large that the analysis becomes impossible or undesirably slow. A simple example of a computationally explosive task is the computation of the factorial of a large number. A factorial, represented by an exclamation mark "!," is a mathematical operation of multiplying a number by each of the integer numbers that comes before it. For example, the value of "4!" would be $4*3*2*1=24$. Factorials are particularly useful in probability theory. For example, the number of possible combinations of arranging the numbers "4, 3, 2, and 1" is 4!, meaning that 24 possible order arrangements exist for those exact four numbers. The probability of randomly selecting any one of the combinations is 1/24, which corresponds to about 0.417%.

However, the factorial representation of large numbers can become computationally explosive. For example, the value of "8,000,000,000!" (the factorial of eight billion) is equal to $(8,000,000,000)*(7,999,999,999)*(7,999,999,998)* \ldots *1$. The multiplication of the first two numbers alone results in about the number $6.4*10e19$, or 6,400,000,000,000,000,000 (or 6.4 quadrillion). Continuing the multiplication all the way to the number "1" causes the final value of "8,000,000,000!" to become truly vast.

Many other different examples of computationally explosive operations exist. For example, comparing the entire genetic sequence of a single human to the genetic sequences of a million other humans would be considered computationally explosive. The problem of the computationally explosive comparison increases exponentially if the genetic sequences of a million humans are compared to the genetic sequences of a second, different million humans. The problem increases exponentially yet again when one desires to compare these factors to other factors, such as diet, environment, and ethnicity, to attempt to determine why certain humans live longer than others.

Thus, numerically solving certain types of computationally explosive operations can be very useful. To date, no satisfactory method exists of numerically solving certain types of computationally explosive operations.

SUMMARY OF THE INVENTION

The illustrative embodiments provide a computer implemented method, apparatus, and computer usable program code for automatically selecting an optimal control cohort. Attributes are selected based on patient data. Treatment cohort records are clustered to form clustered treatment cohorts. Control cohort records are scored to form potential control cohort members. The optimal control cohort is selected by minimizing differences between the potential control cohort members and the clustered treatment cohorts.

The illustrative embodiments also provide for another computer implemented method, computer program product, and data processing system. A datum regarding a first patient is received. A first set of relationships is established. The first set of relationships comprises at least one relationship of the datum to at least one additional datum existing in at least one database. A plurality of cohorts to which the first patient belongs is established based on the first set of relationships. Ones of the plurality of cohorts contain corresponding first data regarding the first patient and corresponding second data regarding a corresponding set of additional information. The corresponding set of additional information is related to the corresponding first data. The plurality of cohorts is clustered according to at least one parameter, wherein a cluster of cohorts is formed. A determination is made of which of at least two cohorts in the cluster are closest to each other. The at least two cohorts can be stored.

In another illustrative embodiment, a second parameter is optimized, mathematically, against a third parameter. The second parameter is associated with a first one of the at least two cohorts. The third parameter is associated with a second one of the at least two cohorts. A result of optimizing can be stored.

In another illustrative embodiment establishing the plurality of cohorts further comprises establishing to what degree a patient belongs in the plurality of cohorts. In yet another illustrative embodiment the second parameter comprises treatments having a highest probability of success for the patient and the third parameter comprises corresponding costs of the treatments.

In another illustrative embodiment, the second parameter comprises treatments having a lowest probability of negative outcome and the second parameter comprises a highest probability of positive outcome. In yet another illustrative embodiment, the at least one parameter comprises a medical diagnosis, wherein the second parameter comprises false positive diagnoses, and wherein the third parameter comprises false negative diagnoses.

In a different illustrative embodiment, a computer implemented method, data processing system, and computer program product for generating synthetic events based on a vast amount of data are provided. A first set of data is received. A second set of data different than the first set of data is received. The first set of data is organized into a first cohort. The second set of data is organized into a second cohort. The first cohort and the second cohort are processed to generate a synthetic event. The synthetic event comprises a third set of data representing a result of a mathematical computation defined by the equation $S(p1) ==> F(p2)$, wherein S comprises a set of input facts with probability $p1$, wherein the set of input facts comprise the first cohort and the second cohort, and wherein F comprises an inferred event with probability $p2$. The term "event" means a particular set of data that represents, encodes, or records at least one of a thing or happening. Each of the first set of data, the second set of data, the first cohort, the second cohort, the synthetic event, and subcomponents thereof all comprise different events. The synthetic event is stored.

In another illustrative embodiment, each corresponding event of the different events is represented as a corresponding pointer. Each corresponding subcomponent of an event is represented as an additional corresponding pointer.

In another illustrative embodiment, performing inference analysis includes performing calculations regarding the first cohort using a first thread executing on a processor having multi-threading functionality and performing calculations regarding the second cohort using a second thread executing on the processor. In still another illustrative embodiment, the first cohort comprises a plurality of data and the second cohort comprises a single datum.

In another illustrative embodiment, the first cohort is derived from a first set of sub-cohorts and wherein the second cohort is derived from a second set of sub-cohorts. In yet another illustrative embodiment, directly comparing the first set of data to the second set of data results in computationally explosive processing. In this illustrative embodiment, the first set of data can represent corresponding gene patterns of corresponding patients in a set of humans, and the second set of data can represent gene patterns of a second set of humans.

The illustrative embodiments can include receiving a third set of data, organizing the third set of data into a third cohort, organizing the synthetic event into a fourth cohort, and processing the first cohort, the second cohort, the third cohort, and the fourth cohort to generate a second synthetic event. The second synthetic event is stored.

This illustrative embodiment can also include processing the first synthetic event and the second synthetic event to generate a third synthetic event. The third synthetic event can also be stored.

In another illustrative embodiment, the first set of data represents gene patterns of individual patients, the second set of data represents diet patterns of a population of individuals in a geographical location, the third set of data represents health records of the individual patients, and the synthetic event represents a probability of that a sub-population of particular ethnic origin will develop cancer. The second synthetic event comprises a probability that the individual patients will develop cancer.

In this particular illustrative embodiment, processing the first synthetic event and the second synthetic event generate a third synthetic event, which can be stored. The third synthetic event can comprise a probability that a specific patient in the individual patients will develop cancer.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

FIG. 24 is a flowchart of a process for generating synthetic events, in accordance with an illustrative embodiment; and FIG. 25 is a flowchart of a process for generating synthetic events, in accordance with an illustrative embodiment.

DETAILED DESCRIPTION OF THE PREFERRED EMBODIMENT

Figure 1:
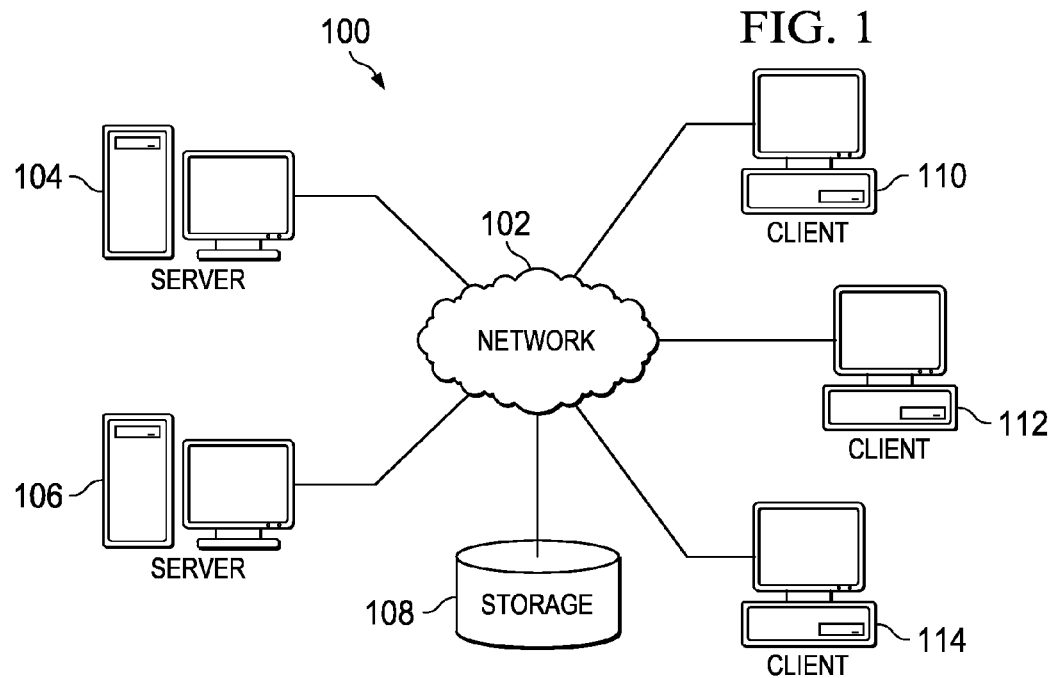
FIG. 1 is a pictorial representation of a data processing system in which an illustrative embodiment may be implemented.
Figure 2:
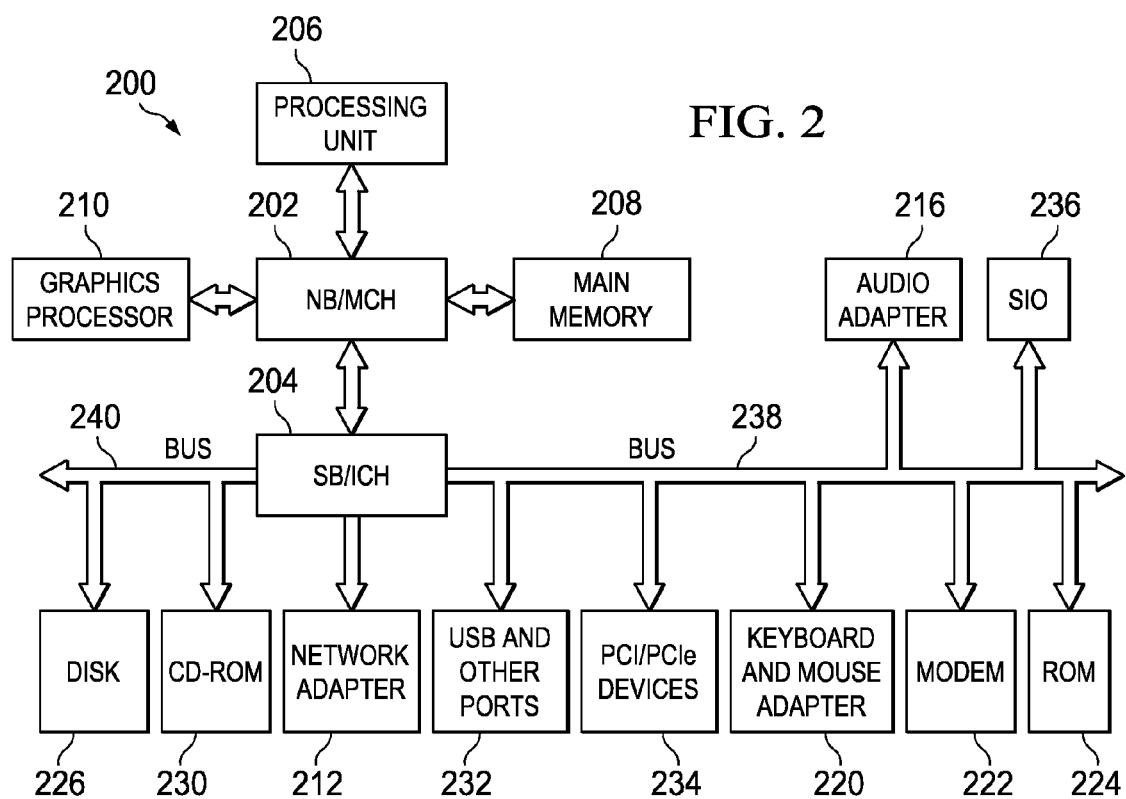
FIG. 2 is a block diagram of a data processing system in which an illustrative embodiment may be implemented.

With reference now to the figures and in particular with reference to FIGS. 1-2, exemplary diagrams of data processing environments are provided in which illustrative embodiments may be implemented. It should be appreciated that FIGS. 1-2 are only exemplary and are not intended to assert or imply any limitation with regard to the environments in which different embodiments may be implemented. Many modifications to the depicted environments may be made.

With reference now to the figures, FIG. 1 depicts a pictorial representation of a network of data processing systems in which an illustrative embodiment may be implemented. Network data processing system 100 is a network of computers in which embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. These clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. Network data processing system 100 may include additional servers, clients, and other devices not shown.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for different embodiments.

With reference now to FIG. 2, a block diagram of a data processing system is shown in which an illustrative embodiment may be implemented. Data processing system 200 is an example of a computer, such as server 104 or client 110 in FIG. 1, in which computer usable code or instructions implementing the processes may be located for the different embodiments.

In the depicted example, data processing system 200 employs a hub architecture including a north bridge and memory controller hub (MCH) 202 and a south bridge and input/output (I/O) controller hub (ICH) 204. Processor 206, main memory 208, and graphics processor 210 are coupled to north bridge and memory controller hub 202. Graphics processor 210 may be coupled to the MCH through an accelerated graphics port (AGP), for example.

In the depicted example, local area network (LAN) adapter 212 is coupled to south bridge and I/O controller hub 204 and audio adapter 216, keyboard and mouse adapter 220, modem 222, read only memory (ROM) 224, universal serial bus (USB) ports and other communications ports 232, and PCI/PCIe devices 234 are coupled to south bridge and I/O controller hub 204 through bus 238, and hard disk drive (HDD) 226 and CD-ROM drive 230 are coupled to south bridge and I/O controller hub 204 through bus 240. PCI/PCIe devices may include, for example, Ethernet adapters, add-in cards, and PC cards for notebook computers. PCI uses a card bus controller, while PCIe does not. ROM 224 may be, for example, a flash binary input/output system (BIOS). Hard disk drive 226 and CD-ROM drive 230 may use, for example, an integrated drive electronics (IDE) or serial advanced technology attachment (SATA) interface. A super I/O (SIO) device 236 may be coupled to south bridge and I/O controller hub 204.

An operating system runs on processor 206 and coordinates and provides control of various components within data processing system 200 in FIG. 2. The operating system may be a commercially available operating system such as Microsoft® Windows® XP (Microsoft and Windows are trademarks of Microsoft Corporation in the United States, other countries, or both). An object oriented programming system, such as the Java™ programming system, may run in conjunction with the operating system and provides calls to the operating system from Java programs or applications executing on data processing system 200 (Java and all Java-based trademarks are trademarks of Sun Microsystems, Inc. in the United States, other countries, or both).

Instructions for the operating system, the object-oriented programming system, and applications or programs are located on storage devices, such as hard disk drive 226, and may be loaded into main memory 208 for execution by processor 206. The processes of the illustrative embodiments may be performed by processor 206 using computer implemented instructions, which may be located in a memory such as, for example, main memory 208, read only memory 224, or in one or more peripheral devices.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. Also, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may be comprised of one or more buses, such as a system bus, an I/O bus and a PCI bus. Of course the bus system may be implemented using any type of communications fabric or architecture that provides for a transfer of data between different components or devices attached to the fabric or architecture. A communications unit may include one or more devices used to transmit and receive data, such as a modem or a network adapter. A memory may be, for example, main memory 208 or a cache such as found in north bridge and memory controller hub 202. A processing unit may include one or more processors or CPUs. The depicted examples in FIGS. 1-2 and above-described examples are not meant to imply architectural limitations. For example, data processing system 200 also may be a tablet computer, laptop computer, or telephone device in addition to taking the form of a PDA.

The illustrative embodiments provide a computer implemented method, apparatus, and computer usable program code for optimizing control cohorts. Results of a clustering process are used to calculate an objective function for selecting an optimal control cohort. A cohort is a group of individuals with common characteristics. Frequently, cohorts are used to test the effectiveness of medical treatments. Treatments are processes, medical procedures, drugs, actions, lifestyle changes, or other treatments prescribed for a specified purpose. A control cohort is a group of individuals that share a common characteristic that does not receive the treatment. The control cohort is compared against individuals or other cohorts that received the treatment to statistically prove the efficacy of the treatment.

The illustrative embodiments provide an automated method, apparatus, and computer usable program code for selecting individuals for a control cohort. To demonstrate a cause and effect relationship, an experiment must be designed to show that a phenomenon occurs after a certain treatment is given to a subject and that the phenomenon does not occur in the absence of the treatment. A properly designed experiment generally compares the results obtained from a treatment cohort against a control cohort which is selected to be practically identical. For most treatments, it is often preferable that the same number of individuals is selected for both the treatment cohort and the control cohort for comparative accuracy. The classical example is a drug trial. The cohort or group receiving the drug would be the treatment cohort, and the group receiving the placebo would be the control cohort. The difficulty is in selecting the two cohorts to be as near to identical as possible while not introducing human bias.

The illustrative embodiments provide an automated method, apparatus, and computer usable program code for selecting a control cohort. Because the features in the different embodiments are automated, the results are repeatable and introduce minimum human bias. The results are independently verifiable and repeatable in order to scientifically certify treatment results.

Figure 3:
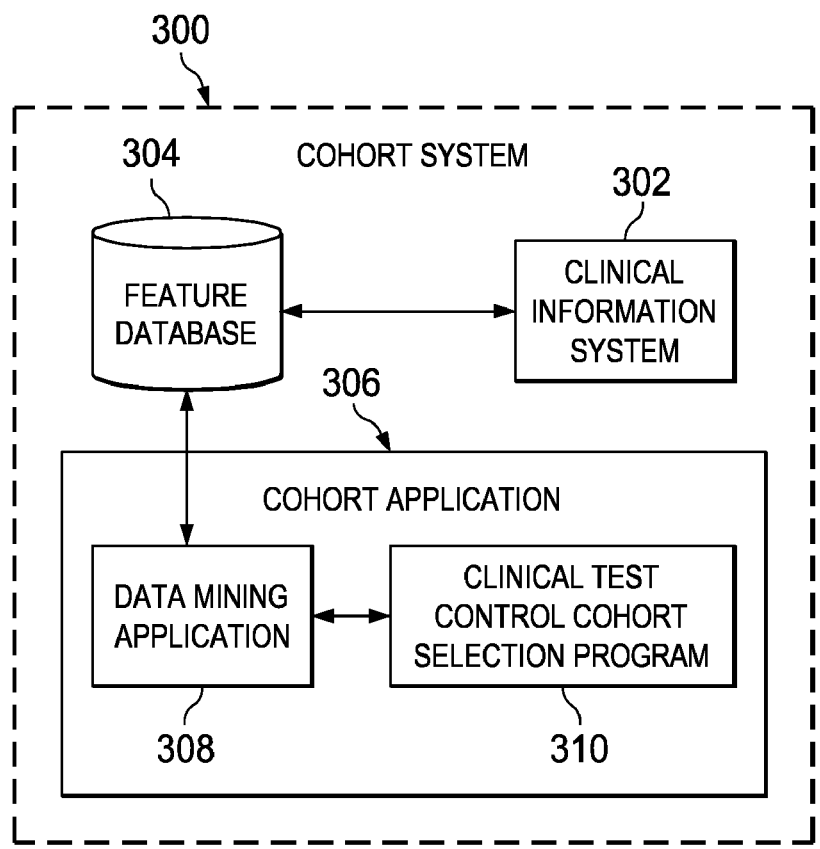
FIG. 3 is a block diagram of a system for generating control cohorts in accordance with an illustrative embodiment.

FIG. 3 is a block diagram of a system for generating control cohorts in accordance with an illustrative embodiment. Cohort system 300 is a system for generating control cohorts. Cohort system 300 includes clinical information system (CIS) 302, feature database 304, and cohort application 306. Each component of cohort system 300 may be interconnected via a network, such as network 102 of FIG. 1. Cohort application 306 further includes data mining application 308 and clinical test control cohort selection program 310.

Clinical information system 302 is a management system for managing patient data. This data may include, for example, demographic data, family health history data, vital signs, laboratory test results, drug treatment history, admission-discharge-treatment (ADT) records, co-morbidities, modality images, genetic data, and other patient data. Clinical information system 302 may be executed by a computing device, such as server 104 or client 110 of FIG. 1. Clinical information system 302 may also include information about population of patients as a whole. Such information may disclose patients who have agreed to participate in medical research but who are not participants in a current study. Clinical information system 302 includes medical records for acquisition, storage, manipulation, and distribution of clinical information for individuals and organizations. Clinical information system 302 is scalable, allowing information to expand as needed. Clinical information system 302 may also include information sourced from pre-existing systems, such as pharmacy management systems, laboratory management systems, and radiology management systems.

Feature database 304 is a database in a storage device, such as storage 108 of FIG. 1. Feature database 304 is populated with data from clinical information system 302. Feature database 304 includes patient data in the form of attributes. Attributes define features, variables, and characteristics of each patient. The most common attributes may include gender, age, disease or illness, and state of the disease.

Cohort application 306 is a program for selecting control cohorts. Cohort application 306 is executed by a computing device, such as server 104 or client 110 of FIG. 1. Data mining application 308 is a program that provides data mining functionality on feature database 304 and other interconnected databases. In one example, data mining application 308 may be a program, such as DB2 Intelligent Miner produced by International Business Machines Corporation. Data mining is the process of automatically searching large volumes of data for patterns. Data mining may be further defined as the non-trivial extraction of implicit, previously unknown, and potentially useful information from data. Data mining application 308 uses computational techniques from statistics, information theory, machine learning, and pattern recognition.

Particularly, data mining application 308 extracts useful information from feature database 304. Data mining application 308 allows users to select data, analyze data, show patterns, sort data, determine relationships, and generate statistics. Data mining application 308 may be used to cluster records in feature database 304 based on similar attributes.

Data mining application 308 searches the records for attributes that most frequently occur in common and groups the related records or members accordingly for display or analysis to the user. This grouping process is referred to as clustering. The results of clustering show the number of detected clusters and the attributes that make up each cluster. Clustering is further described with respect to FIGS. 4A-4B.

For example, data mining application 308 may be able to group patient records to show the effect of a new sepsis blood infection medicine. Currently, about 35 percent of all patients with the diagnosis of sepsis die. Patients entering an emergency department of a hospital who receive a diagnosis of sepsis, and who are not responding to classical treatments, may be recruited to participate in a drug trial. A statistical control cohort of similarly ill patients could be developed by cohort system 300, using records from historical patients, patients from another similar hospital, and patients who choose not to participate. Potential features to produce a clustering model could include age, co-morbidities, gender, surgical procedures, number of days of current hospitalization, O2 blood saturation, blood pH, blood lactose levels, bilirubin levels, blood pressure, respiration, mental acuity tests, and urine output.

Data mining application 308 may use a clustering technique or model known as a Kohonen feature map neural network or neural clustering. Kohonen feature maps specify a number of clusters and the maximum number of passes through the data. The number of clusters must be between one and the number of records in the treatment cohort. The greater the number of clusters, the better the comparisons can be made between the treatment and the control cohort. Clusters are natural groupings of patient records based on the specified features or attributes. For example, a user may request that data mining application 308 generate eight clusters in a maximum of ten passes. The main task of neural clustering is to find a center for each cluster. The center is also called the cluster prototype. Scores are generated based on the distance between each patient record and each of the cluster prototypes. Scores closer to zero have a higher degree of similarity to the cluster prototype. The higher the score, the more dissimilar the record is from the cluster prototype.

All inputs to a Kohonen feature map must be scaled from 0.0 to 1.0. In addition, categorical values must be converted into numeric codes for presentation to the neural network. Conversions may be made by methods that retain the ordinal order of the input data, such as discrete step functions or bucketing of values. Each record is assigned to a single cluster, but by using data mining application 308, a user may determine a record's Euclidean dimensional distance for all cluster prototypes. Clustering is performed for the treatment cohort. Clinical test control cohort selection program 310 minimizes the sum of the Euclidean distances between the individuals or members in the treatment cohorts and the control cohort. Clinical test control cohort selection program 310 may incorporate an integer programming model, such as integer programming system 806 of FIG. 8. This program may be programmed in International Business Machine Corporation products, such as Mathematical Programming System eXtended (MPSX), the IBM Optimization Subroutine Library, or the open source GNU Linear Programming Kit. The illustrative embodiments minimize the summation of all records/cluster prototype Euclidean distances from the potential control cohort members to select the optimum control cohort.

Figure 4A:
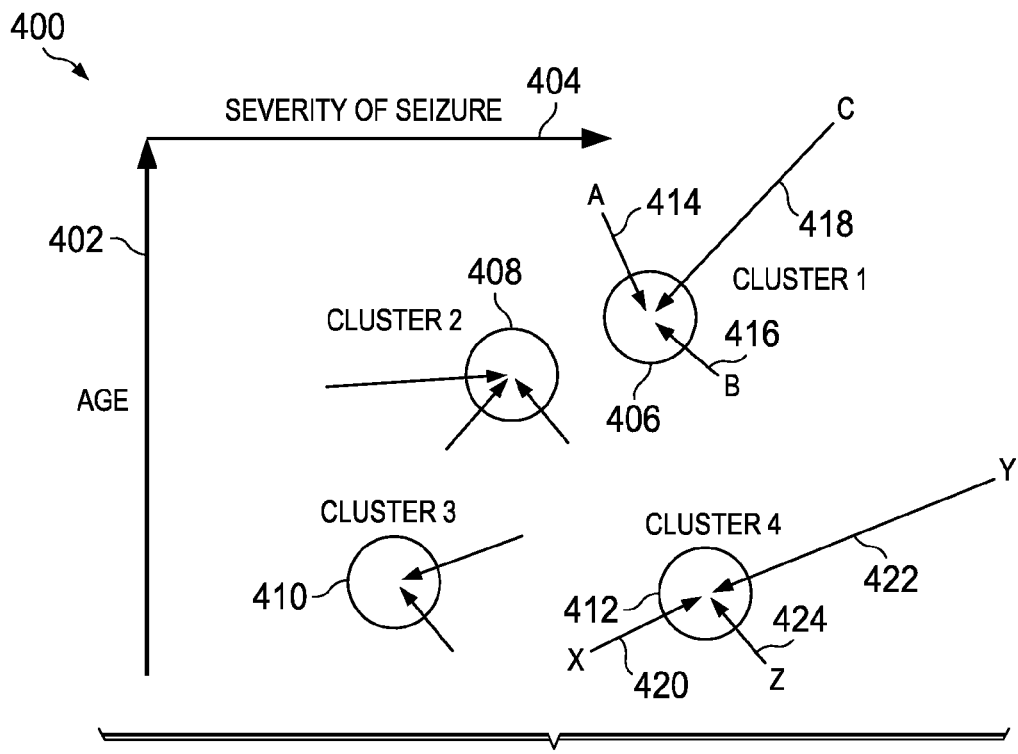
FIGS. 4A-4B are graphical illustrations of clustering in accordance with an illustrative embodiment.
Figure 4B:
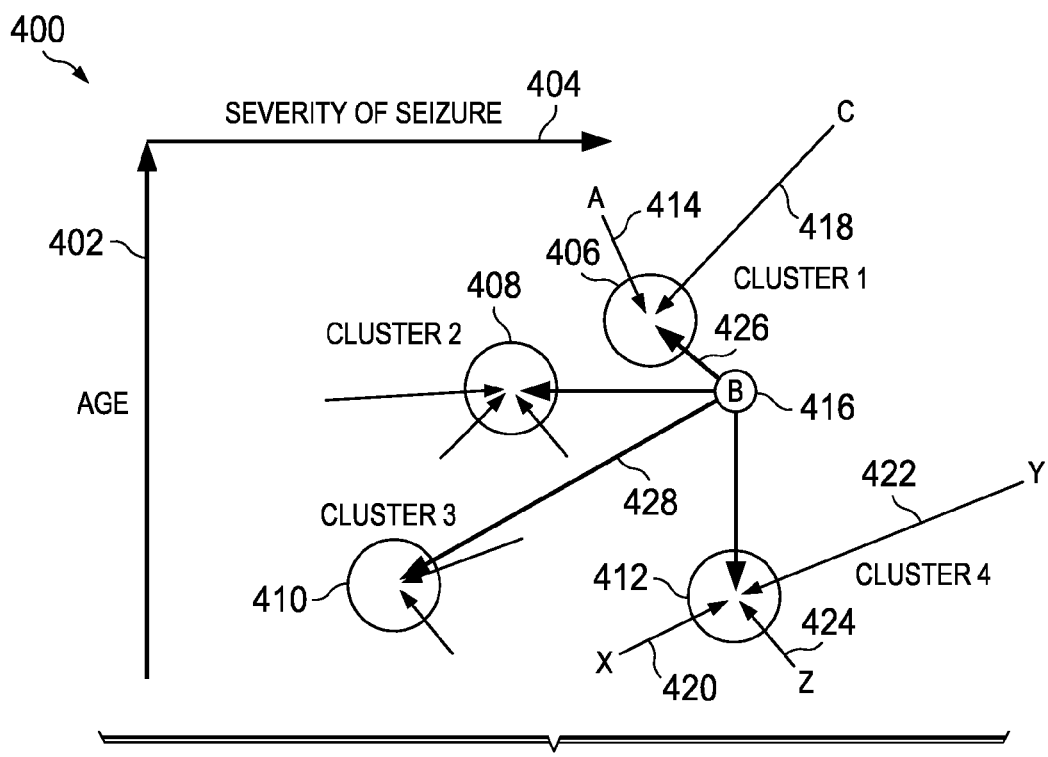

FIGS. 4A-4B are graphical illustrations of clustering in accordance with an illustrative embodiment. Feature map 400 of FIG. 4A is a self-organizing map (SOM) and is a subtype of artificial neural networks. Feature map 400 is trained using unsupervised learning to produce low-dimensional representation of the training samples while preserving the topological properties of the input space. This makes feature map 400 especially useful for visualizing high-dimensional data, including cohorts and clusters.

In one illustrative embodiment, feature map 400 is a Kohonen Feature Map neural network. Feature map 400 uses a process called self-organization to group similar patient records together. Feature map 400 may use various dimensions. In this example, feature map 400 is a two-dimensional feature map including age 402 and severity of seizure 404. Feature map 400 may include as many dimensions as there are features, such as age, gender, and severity of illness. Feature map 400 also includes cluster 1 406, cluster 2 408, cluster 3 410, and cluster 4 412. The clusters are the result of using feature map 400 to group individual patients based on the features. The clusters are self-grouped local estimates of all data or patients being analyzed based on competitive learning. When a training sample of patients is analyzed by data mining application 308 of FIG. 3, each patient is grouped into clusters where the clusters are weighted functions that best represent natural divisions of all patients based on the specified features.

The user may choose to specify the number of clusters and the maximum number of passes through the data. These parameters control the processing time and the degree of granularity used when patient records are assigned to clusters. The primary task of neural clustering is to find a center for each cluster. The center is called the cluster prototype. For each record in the input patient data set, the neural clustering data mining algorithm computes the cluster prototype that is the closest to the records. For example, patient record A 414, patient record B 416, and patient record C 418 are grouped into cluster 1 406. Additionally, patient record X 420, patient record Y 422, and patient record Z 424 are grouped into cluster 4 412.

FIG. 4B further illustrates how the score for each data record is represented by the Euclidean distance from the cluster prototype. The higher the score, the more dissimilar the record is from the particular cluster prototype. With each pass over the input patient data, the centers are adjusted so that a better quality of the overall clustering model is reached. To score a potential control cohort for each patient record, the Euclidian distance is calculated from each cluster prototype. This score is passed along to an integer programming system in clinical test control cohort selection program 310 of FIG. 3. The scoring of each record is further shown by integer programming system 806 of FIG. 8 below.

For example, patient B 416 is scored into the cluster prototype or center of cluster 1 406, cluster 2 408, cluster 3 410 and cluster 4 412. A Euclidean distance between patient B 416 and cluster 1 406, cluster 2 408, cluster 3 410 and cluster 4 412 is shown. In this example, distance 1 426, separating patient B 416 from cluster 1 406, is the closest. Distance 3 428, separating patient B 416 from cluster 3 410, is the furthest. These distances indicate that cluster 1 406 is the best fit.

Figure 5:
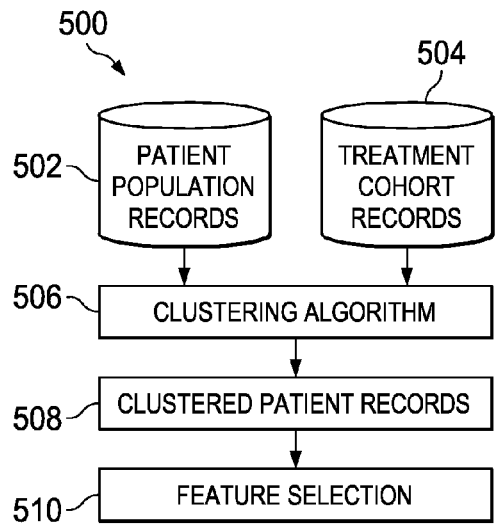
FIG. 5 is a block diagram illustrating information flow for feature selection in accordance with an illustrative embodiment.

FIG. 5 is a block diagram illustrating information flow for feature selection in accordance with an illustrative embodiment. The block diagram of FIG. 5 may be implemented in cohort application 306 of FIG. 3. Feature selection system 500 includes various components and modules used to perform variable selection. The features selected are the features or variables that have the strongest effect in cluster assignment. For example, blood pressure and respiration may be more important in cluster assignment than patient gender. Feature selection system 500 may be used to perform step 902 of FIG. 9. Feature selection system 500 includes patient population records 502, treatment cohort records 504, clustering algorithm 506, clustered patient records 508, and produces feature selection 510.

Patient population records 502 are all records for patients who are potential control cohort members. Patient population records 502 and treatment cohort records 504 may be stored in a database or system, such as clinical information system 302 of FIG. 3. Treatment cohort records 504 are all records for the selected treatment cohort. The treatment cohort is selected based on the research, study, or other test that is being performed.

Clustering algorithm 506 uses the features from treatment cohort records 504 to group patient population records in order to form clustered patient records 508. Clustered patient records 508 include all patients grouped according to features of treatment cohort records 504. For example, clustered patient records 508 may be clustered by a clustering algorithm according to gender, age, physical condition, genetics, disease, disease state, or any other quantifiable, identifiable, or other measurable attribute. Clustered patient records 508 are clustered using feature selection 510.

Feature selection 510 is the features and variables that are most important for a control cohort to mirror the treatment cohort. For example, based on the treatment cohort, the variables in feature selection 510 most important to match in the treatment cohort may be age 402 and severity of seizure 404 as shown in FIG. 4.

Figure 6:
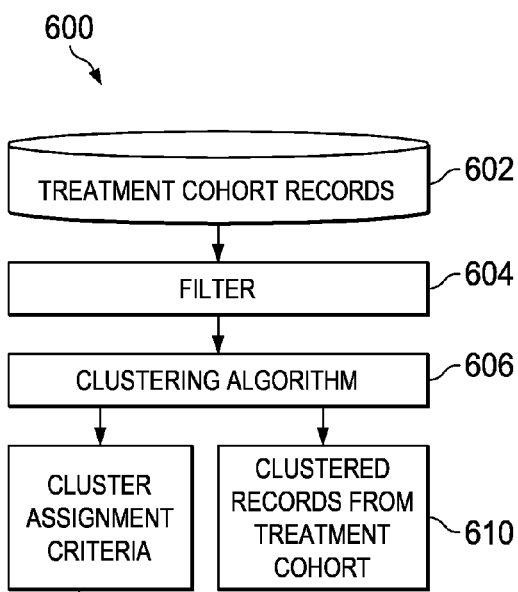
FIG. 6 is a block diagram illustrating information flow for clustering records in accordance with an illustrative embodiment.

FIG. 6 is a block diagram illustrating information flow for clustering records in accordance with an illustrative embodiment. The block diagram of FIG. 6 may be implemented in cohort application 306 of FIG. 3. Cluster system 600 includes various components and modules used to cluster assignment criteria and records from the treatment cohort. Cluster system 600 may be used to perform step 904 of FIG. 9. Cluster system 600 includes treatment cohort records 602, filter 604, clustering algorithm 606, cluster assignment criteria 608, and clustered records from treatment cohort 610. Filter 604 is used to eliminate any patient records that have significant co-morbidities that would by itself eliminate inclusion in a drug trial. Co-morbidities are other diseases, illnesses, or conditions in addition to the desired features. For example, it may be desirable to exclude results from persons with more than one stroke from the statistical analysis of a new heart drug.

Treatment cohort records 602 are the same as treatment cohort records 504 of FIG. 5. Filter 604 filters treatment cohort records 602 to include only selected variables such as those selected by feature selection 510 of FIG. 5.

Clustering algorithm 606 is similar to clustering algorithm 506 of FIG. 5. Clustering algorithm 606 uses the results from filter 604 to generate cluster assignment criteria 608 and clustered records from treatment cohort 610. For example, patient A 414, patient B 416, and patient C 418 are assigned into cluster 1 406, all of FIGS. 4A-4B. Clustered records from treatment cohort 610 are the records for patients in the treatment cohort. Every patient is assigned to a primary cluster, and a Euclidean distance to all other clusters is determined. The distance is a distance, such as distance 426, separating patient B 416 and the center or cluster prototype of cluster 1 406 of FIG. 4B. In FIG. 4B, patient B 416 is grouped into the primary cluster of cluster 1 406 because of proximity. Distances to cluster 2 408, cluster 3 410, and cluster 4 412 are also determined.

Figure 7:
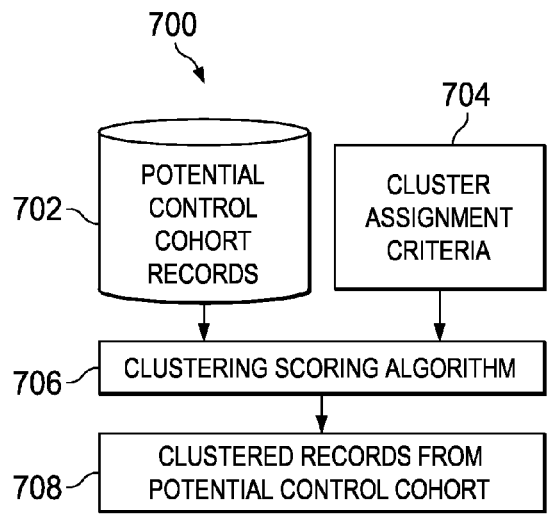
FIG. 7 is a block diagram illustrating information flow for clustering records for a potential control cohort in accordance with an illustrative embodiment.

FIG. 7 is a block diagram illustrating information flow for clustering records for a potential control cohort in accordance with an illustrative embodiment. The block diagram of FIG. 7 may be implemented in cohort application 306 of FIG. 3. Cluster system 700 includes various components and modules used to cluster potential control cohorts. Cluster system 700 may be used to perform step 906 of FIG. 9. Cluster system 700 includes potential control cohort records 702, cluster assignment criteria 704, clustering scoring algorithm 706, and clustered records from potential control cohort 708.

Potential control cohort records 702 are the records from patient population records, such as patient population records 502 of FIG. 5 that may be selected to be part of the control cohort. For example, potential control cohort records 702 do not include patient records from the treatment cohort. Clustering scoring algorithm 706 uses cluster assignment criteria 704 to generate clustered records from potential control cohort 708. Cluster assignment criteria are the same as cluster assignment criteria 608 of FIG. 6.

Figure 8:
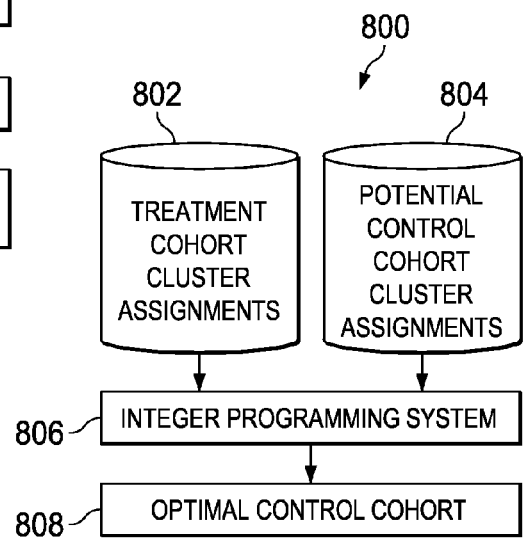
FIG. 8 is a block diagram illustrating information flow for generating an optimal control cohort in accordance with an illustrative embodiment.

FIG. 8 is a block diagram illustrating information flow for generating an optimal control cohort in accordance with an illustrative embodiment. Cluster system 800 includes various components and modules used to cluster the optimal control cohort. Cluster system 800 may be used to perform step 908 of FIG. 9. Cluster system 800 includes treatment cohort cluster assignments 802, potential control cohort cluster assignments 804, integer programming system 806, and optimal control cohort 808. The cluster assignments indicate the treatment and potential control cohort records that have been grouped to that cluster.

0-1 Integer programming is a special case of integer programming where variables are required to be 0 or 1, rather than some arbitrary integer. The illustrative embodiments use integer programming system 806 because a patient is either in the control group or is not in the control group. Integer programming system 806 selects the optimum patients for optimal control cohort 808 that minimize the differences from the treatment cohort. The objective function of integer programming system 806 is to minimize the absolute value of the sum of the Euclidian distance of all possible control cohorts compared to the treatment cohort cluster prototypes. 0-1 Integer programming typically utilizes many well-known techniques to arrive at the optimum solution in far less time than would be required by complete enumeration. Patient records may be used zero or one time in the control cohort. Optimal control cohort 808 may be displayed in a graphical format to demonstrate the rank and contribution of each feature/variable for each patient in the control cohort.

Figure 9:
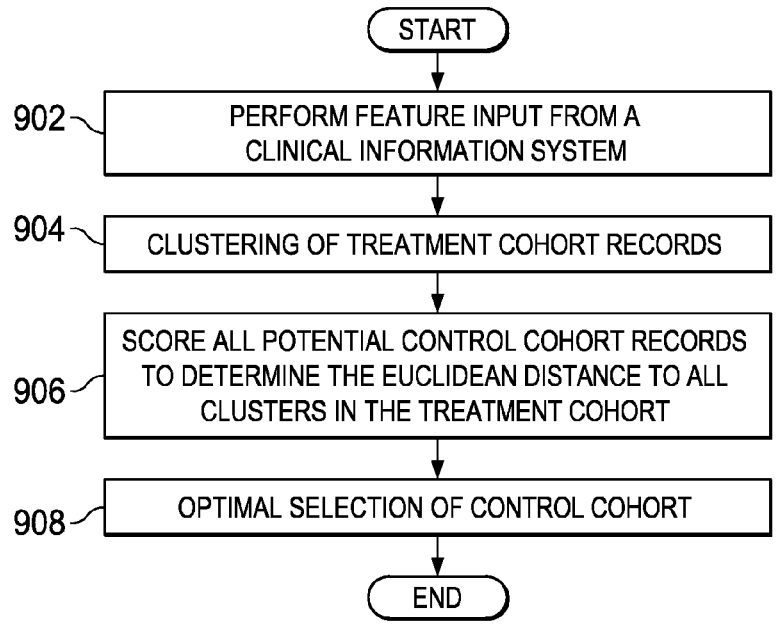
FIG. 9 is a process for optimal selection of control cohorts in accordance with an illustrative embodiment.

FIG. 9 is a flowchart of a process for optimal selection of control cohorts in accordance with an illustrative embodiment. The process of FIG. 9 may be implemented in cohort system 300 of FIG. 3. The process first performs feature input from a clinical information system (step 902). In step 902, the process step moves every potential patient feature data stored in a clinical data warehouse, such as clinical information system 302 of FIG. 3. During step 902, many more variables are input than will be used by the clustering algorithm. These extra variables will be discarded by feature selection 510 of FIG. 5.

Some variables, such as age and gender, will need to be included in all clustering models. Other variables are specific to given diseases like Gleason grading system to help describe the appearance of the cancerous prostate tissue. Most major diseases have similar scales measuring the severity and spread of a disease. In addition to variables describing the major disease focus of the disease, most patients have co-morbidities. These might be conditions like diabetes, high blood pressure, stroke, or other forms of cancer. These comormidities may skew the statistical analysis so the control cohort must carefully select patients who well mirror the treatment cohort.

Next, the process clusters treatment cohort records (step 904). Next, the process scores all potential control cohort records to determine the Euclidean distance to all clusters in the treatment cohort (step 906). Step 904 and 906 may be performed by data mining application 308 based on data from feature database 304 and clinical information system 302 all of FIG. 3. Next, the process performs optimal selection of a control cohort (step 908) with the process terminating thereafter. Step 908 may be performed by clinical test control cohort selection program 310 of FIG. 3. The optimal selection is made based on the score calculated during step 906. The scoring may also involving weighting. For example, if a record is an equal distance between two clusters, but one cluster has more records the record may be clustered in the cluster with more records. During step 908, names, unique identifiers, or encoded indices of individuals in the optimal control cohort are displayed or otherwise provided.

In one illustrative scenario, a new protocol has been developed to reduce the risk of re-occurrence of congestive heart failure after discharging a patient from the hospital. A pilot program is created with a budget sufficient to allow 600 patients in the treatment and control cohorts. The pilot program is designed to apply the new protocol to a treatment cohort of patients at the highest risk of re-occurrence.

The clinical selection criteria for inclusion in the treatment cohort specifies that each individual:

1. Have more than one congestive heart failure related admission during the past year.
2. Have fewer than 60 days since the last congestive heart failure related admission.
3. Be 45 years or older.

Each of these attributes may be determined during feature selection of step 902. The clinical criteria yields 296 patients for the treatment cohort, so 296 patients are needed for the control cohort. The treatment cohort and control cohort are selected from patient records stored in feature database 304 or clinical information system 302 of FIG. 3.

Originally, there were 2,927 patients available for the study. The treatment cohort reduces the patient number to 2,631 unselected patients. Next, the 296 patients of the treatment cohort are clustered during step 904. The clustering model determined during step 904 is applied to the 2,631 unselected patients to score potential control cohort records in step 906. Next, the process selects the best matching 296 patients for the optimal selection of a control cohort in step 908. The result is a group of 592 patients divided between treatment and control cohorts who best fit the clinical criteria. The results of the control cohort selection are repeatable and defendable.

Thus, the illustrative embodiments provide a computer implemented method, apparatus, and computer usable program code for optimizing control cohorts. The control cohort is automatically selected from patient records to minimize the differences between the treatment cohort and the control cohort. The results are automatic and repeatable with the introduction of minimum human bias.

ADDITIONAL ILLUSTRATIVE EMBODIMENTS

The illustrative embodiments also provide for a computer implemented method, apparatus, and computer usable program code for automatically selecting an optimal control cohort. Attributes are selected based on patient data. Treatment cohort records are clustered to form clustered treatment cohorts. Control cohort records are scored to form potential control cohort members. The optimal control cohort is selected by minimizing differences between the potential control cohort members and the clustered treatment cohorts.

The illustrative embodiments provide for a computer implemented method for automatically selecting an optimal control cohort, the computer implemented method comprising: selecting attributes based on patient data; clustering of treatment cohort records to form clustered treatment cohorts; scoring control cohort records to form potential control cohort members; and selecting the optimal control cohort by minimizing differences between the potential control cohorts members and the clustered treatment cohorts.

In this illustrative example, the patient data can be stored in a clinical database. The attributes can be any of features, variables, and characteristics. The clustered treatment cohorts can show a number of clusters and characteristics of each of the number of clusters. The attributes can include gender, age, disease state, genetics, and physical condition. Each patient record can be scored to calculate the Euclidean distance to all clusters. A user can specify the number of clusters for the clustered treatment cohorts and a number of search passes through the patient data to generate the number of clusters. The selecting attributes and the clustering steps can be performed by a data mining application, wherein the selecting the optimal control cohort step is performed by a 0-1 integer programming model.

In another illustrative embodiment, the selecting step further can further comprise: searching the patient data to determine the attributes that most strongly differentiate assignment of patient records to particular clusters. In another illustrative embodiment the scoring step comprises: scoring all patient records by computing a Euclidean distance to cluster prototypes of all treatment cohorts. In another illustrative embodiment the clustering step further comprises: generating a feature map to form the clustered treatment cohorts.

In another illustrative embodiment, any of the above methods can include providing names, unique identifiers, or encoded indices of individuals in the optimal control cohort. In another illustrative embodiment, the feature map is a Kohonen feature map.

The illustrative embodiments also provide for an optimal control cohort selection system comprising: an attribute database operatively connected to a clinical information system for storing patient records including attributes of patients; a server operably connected to the attribute database wherein the server executes a data mining application and a clinical control cohort selection program wherein the data mining application selects specified attributes based on patient data, clusters treatment cohort records based on the specified attributes to form clustered treatment cohorts, and clusters control cohort records based on the specified attributes to form clustered control cohorts; and wherein the clinical control cohort selection program selects the optimal control cohort by minimizing differences between the clustered control cohorts and the clustered treatment cohorts.

In this illustrative embodiment, the clinical information system includes information about populations of patients wherein the information is accessed by the server. In another illustrative embodiment, the data mining application is IBM DB2 Intelligent Miner.

The illustrative embodiments also provide for a computer program product comprising a computer usable medium including computer usable program code for automatically selecting an optimal control cohort, the computer program product comprising: computer usable program code for selecting attributes based on patient data; computer usable program code for clustering of treatment cohort records to form clustered treatment cohorts; computer usable program code for scoring control cohort records to form potential control cohort members; and computer usable program code for selecting the optimal control cohort by minimizing differences between the potential control cohorts members and the clustered treatment cohorts.

In this illustrative embodiment, the computer program product can also include computer usable program code for scoring all patient records in a self organizing map by computing a Euclidean distance to cluster prototypes of all treatment cohorts; and computer usable program code for generating a feature map to form the clustered treatment cohorts. In another illustrative embodiment, the computer program product can also include computer usable program code for specifying a number of clusters for the clustered treatment cohorts and a number of search passes through the patient data to generate the number of clusters. In yet another illustrative embodiment, the computer usable program code for selecting further comprises: computer usable program code for searching the patient data to determine the attributes that most strongly differentiate assignment of patient records to particular clusters.

Figure 10:
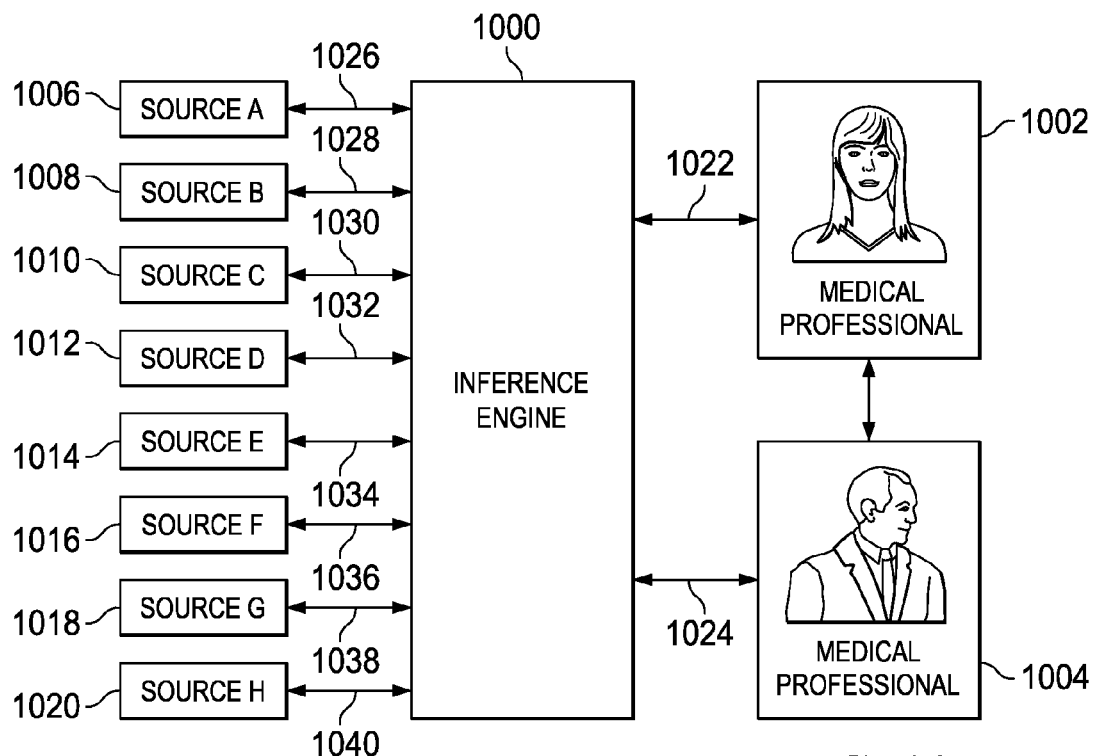
FIG. 10 is a block diagram illustrating an inference engine used for generating an inference not already present in one or more databases being accessed to generate the inference, in accordance with an illustrative embodiment.

Returning to the figures, FIG. 10 is a block diagram illustrating an inference engine used for generating an inference not already present in one or more databases being accessed to generate the inference, in accordance with an illustrative embodiment. The method shown in FIG. 10 can be implemented by one or more users using one or more data processing systems, such as server 104, server 106, client 110, client 112, and client 114 in FIG. 1 and data processing system 200 shown in FIG. 2, which communicate over a network, such as network 102 shown in FIG. 1. Additionally, the illustrative embodiments described in FIG. 10 and throughout the specification can be implemented using these data processing systems in conjunction with inference engine 1000. Inference engine 1000 has been developed during our past work, including our previously filed and published patent applications.

FIG. 10 shows a solution to the problem of allowing different medical professionals to both find and consider relevant information from a truly massive amount of divergent data. Inference engine 1000 allows medical professional 1002 and medical professional 1004 to find relevant information based on one or more queries and, more importantly, cause inference engine 1000 to assign probabilities to the likelihood that certain inferences can be made based on the query. The process is massively recursive in that every piece of information added to the inference engine can cause the process to be re-executed. An entirely different result can arise based on new information. Information can include the fact that the query itself was simply made. Information can also include the results of the query, or information can include data from any one of a number of sources.

Additionally, inference engine 1000 receives as much information as possible from as many different sources as possible. Thus, inference engine 1000 serves as a central repository of information from medical professional 1002, medical professional 1004, source A 1006, source B 1008, source C 1010, source D 1012, source E 1014, source F 1016, source G 1018, and source H 1020. In an illustrative embodiment, inference engine 1000 can also input data into each of those sources. Arrows 1022, arrows 1024, arrows 1026, arrows 1028, arrows 1030, arrows 1032, arrows 1034, arrows 1036, arrows 1038, and arrows 1040 are all bidirectional arrows to indicate that inference engine 1000 is capable of both receiving and inputting information from and to all sources of information. However, not all sources are necessarily capable of receiving data; in these cases, inference engine 1000 does not attempt to input data into the corresponding source.

In an illustrative example relating to generating an inference relating to the provision of healthcare, either or both of medical professional 1002 or medical professional 1004 are attempting to diagnose a patient having symptoms that do not exactly match any known disease or medical condition. Either or both of medical professional 1002 or medical professional 1004 can submit queries to inference engine 1000 to aid in the diagnosis. The queries are based on symptoms that the patient is exhibiting, and possibly also based on guesses and information known to the doctors. Inference engine 1000 can access numerous databases, such as any of sources A through H, and can even take into account that both medical professional 1002 and medical professional 1004 are both making similar queries, all in order to generate a probability of an inference that the patient suffers from a particular medical condition, a set of medical conditions, or even a new (emerging) medical condition. Inference engine 1000 greatly increases the odds that a correct diagnosis will be made by eliminating or reducing incorrect diagnoses.

Thus, inference engine 1000 is adapted to receive a query regarding a fact, use the query as a frame of reference, use a set of rules to generate a second set of rules to be applied when executing the query, and then execute the query using the second set of rules to compare data in inference engine 1000 to create probability of an inference. The probability of the inference is stored as additional data in the database and is reported to the medical professional or medical professionals submitting the query. Inference engine 1000 can prompt one or both of medical professional 1002 and medical professional 1004 to contact each other for possible consultation.

Thus, continuing the above example, medical professional 1002 submits a query to inference engine 1000 to generate probabilities that a patient has a particular condition or set of conditions. Inference engine 1000 uses these facts or concepts as a frame of reference. A frame of reference is an anchor datum or set of data that is used to limit which data are searched in inference engine 1000. The frame of reference also helps define the search space. The frame of reference also is used to determine to what rules the searched data will be subject. Thus, when the query is executed, sufficient processing power will be available to make inferences.

The frame of reference is used to establish a set of rules for generating a second set of rules. For example, the set of rules could be used to generate a second set of rules that include searching all information related to the enumerated symptoms, all information related to similar symptoms, and all information related to medical experts known to specialize in conditions possibly related to the enumerated symptoms, but (in this example only) no other information. The first set of rules also creates a rule that specifies that only certain interrelationships between these data sets will be searched.

Inference engine 1000 uses the second set of rules when the query is executed. In this case, the query compares the relevant data in the described classes of information. In comparing the data from all sources, the query matches symptoms to known medical conditions. Inference engine 1000 then produces a probability of an inference. The inference, in this example, is that the patient suffers from both Parkinson's disease and Alzheimer's disease, but also may be exhibiting a new medical condition. Possibly thousands of other inferences matching other medical conditions are also made; however, only the medical conditions above a defined (by the user or by inference engine 1000 itself) probability are presented.

In this case, the medical professional desires to narrow the search because the medical professional cannot pick out the information regarding the possible new condition from the thousands of other inferences.

Continuing the example, the above inference and the probability of inference are re-inputted into inference engine 1000 and an additional query is submitted to determine an inference regarding a probability of a new diagnosis. Again, inference engine 1000 establishes the facts of the query as a frame of reference and then uses a set of rules to determine another set of rules to be applied when executing the query. This time, the query will compare disease states identified in the first query. The query will also compare new information or databases relating to those specific diseases.

The query is again executed using the second set of rules. The query compares all of the facts and creates a probability of a second inference. In this illustrative example, the probability of a second inference is a high chance that, based on the new search, the patient actually has Alzheimer's disease and another, known, neurological disorder that better matches the symptoms. Medical professional 1002 then uses this inference to design a treatment plan for the patient.

Inference engine 1000 includes one or more divergent data. The plurality of divergent data includes a plurality of cohort data. Each datum of the database is conformed to the dimensions of the database. Each datum of the plurality of data has associated metadata and an associated key. A key uniquely identifies an individual datum. A key can be any unique identifier, such as a series of numbers, alphanumeric characters, other characters, or other methods of uniquely identifying objects. The associated metadata includes data regarding cohorts associated with the corresponding datum, data regarding hierarchies associated with the corresponding datum, data regarding a corresponding source of the datum, and data regarding probabilities associated with integrity, reliability, and importance of each associated datum.

Figure 11:
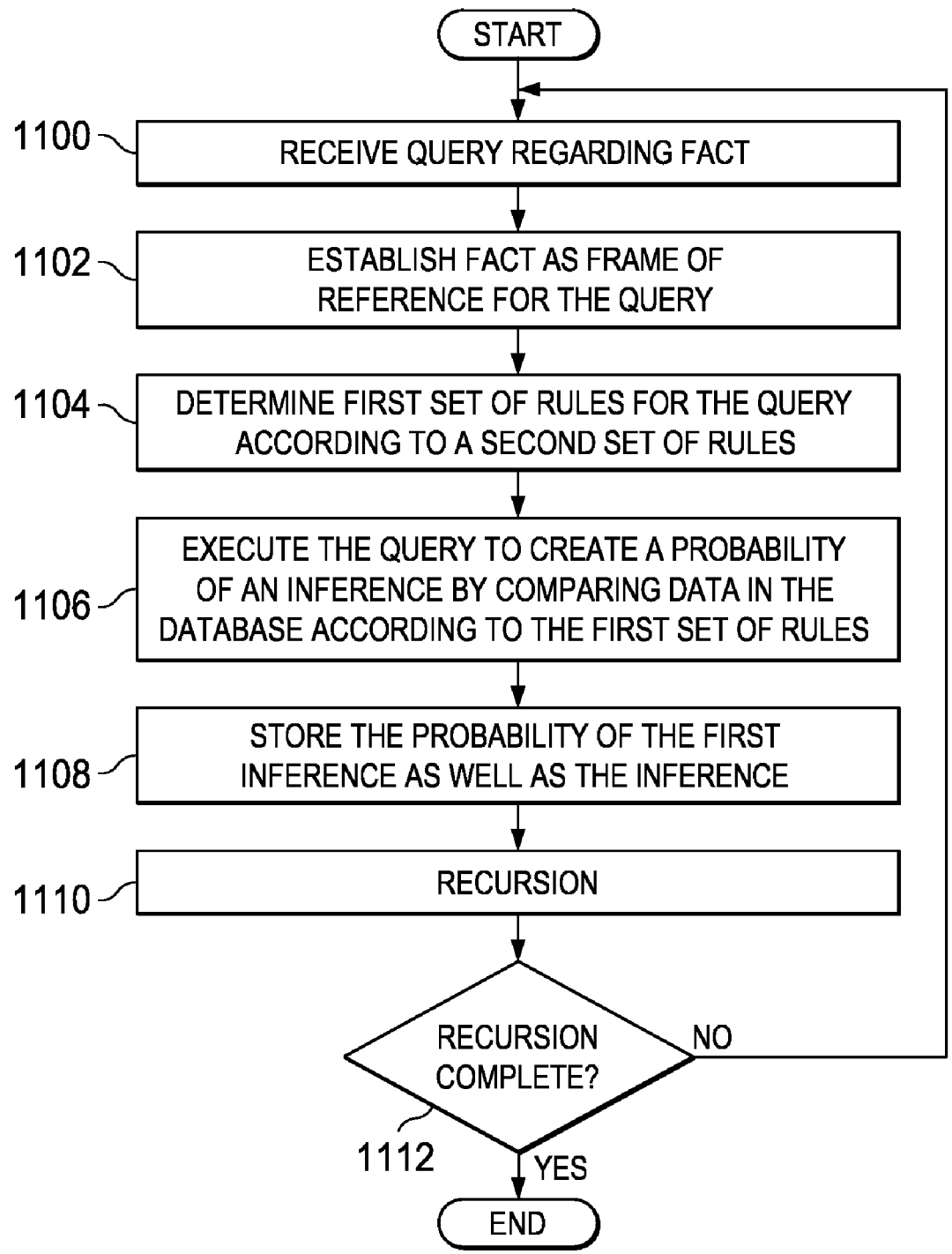
FIG. 11 is a flowchart illustrating execution of a query in a database to establish a probability of an inference based on data contained in the database, in accordance with an illustrative embodiment.

FIG. 11 is a flowchart illustrating execution of a query in a database to establish a probability of an inference based on data contained in the database, in accordance with an illustrative embodiment. The process shown in FIG. 11 can be implemented using inference engine 1000 and can be implemented in a single data processing system or across multiple data processing systems connected by one or more networks. Whether implemented in a single data processing system or across multiple data processing systems, taken together all data processing systems, hardware, software, and networks are together referred to as a system. The system implements the process.

The process begins as the system receives a query regarding a fact (step 1100). The system establishes the fact as a frame of reference for the query (step 1102). The system then determines a first set of rules for the query according to a second set of rules (step 1104). The system executes the query according to the first set of rules to create a probability of an inference by comparing data in the database (step 1106). The system then stores the probability of the first inference and also stores the inference (step 1108).

The system then performs a recursion process (step 1110). During the recursion process steps 1100 through 1108 are repeated again and again, as each new inference and each new probability becomes a new fact that can be used to generate a new probability and a new inference. Additionally, new facts can be received in central database 400 during this process, and those new facts also influence the resulting process. Each conclusion or inference generated during the recursion process can be presented to a user, or only the final conclusion or inference made after step 1112 can be presented to a user, or a number of conclusions made prior to step 1112 can be presented to a user.

The system then determines whether the recursion process is complete (step 1112). If recursion is not complete, the process between steps 1100 and 1110 continues. If recursion is complete, the process terminates.

Figure 12A:
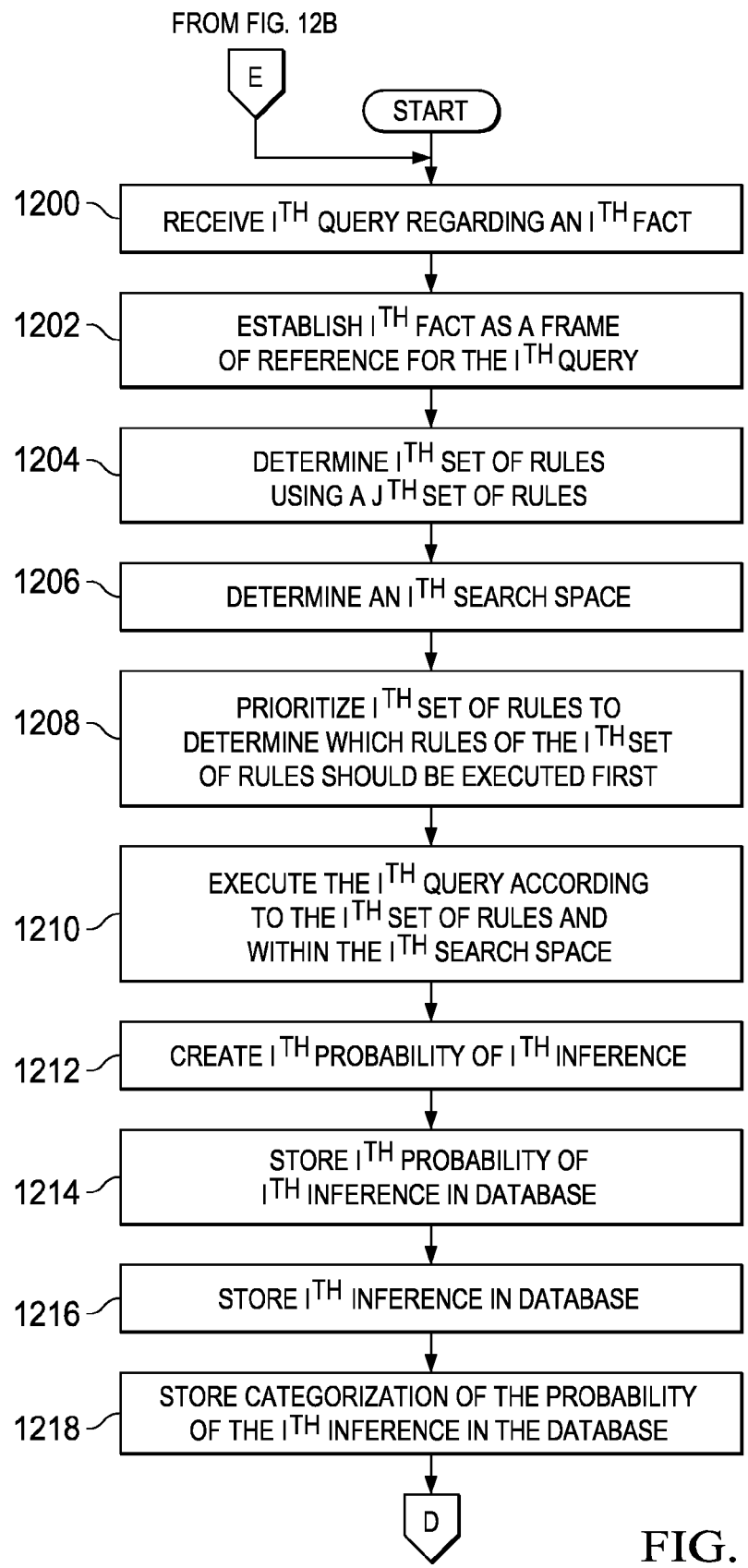
FIGS. 12A and 12B are a flowchart illustrating execution of a query in a database to establish a probability of an inference based on data contained in the database, in accordance with an illustrative embodiment.
Figure 12B:
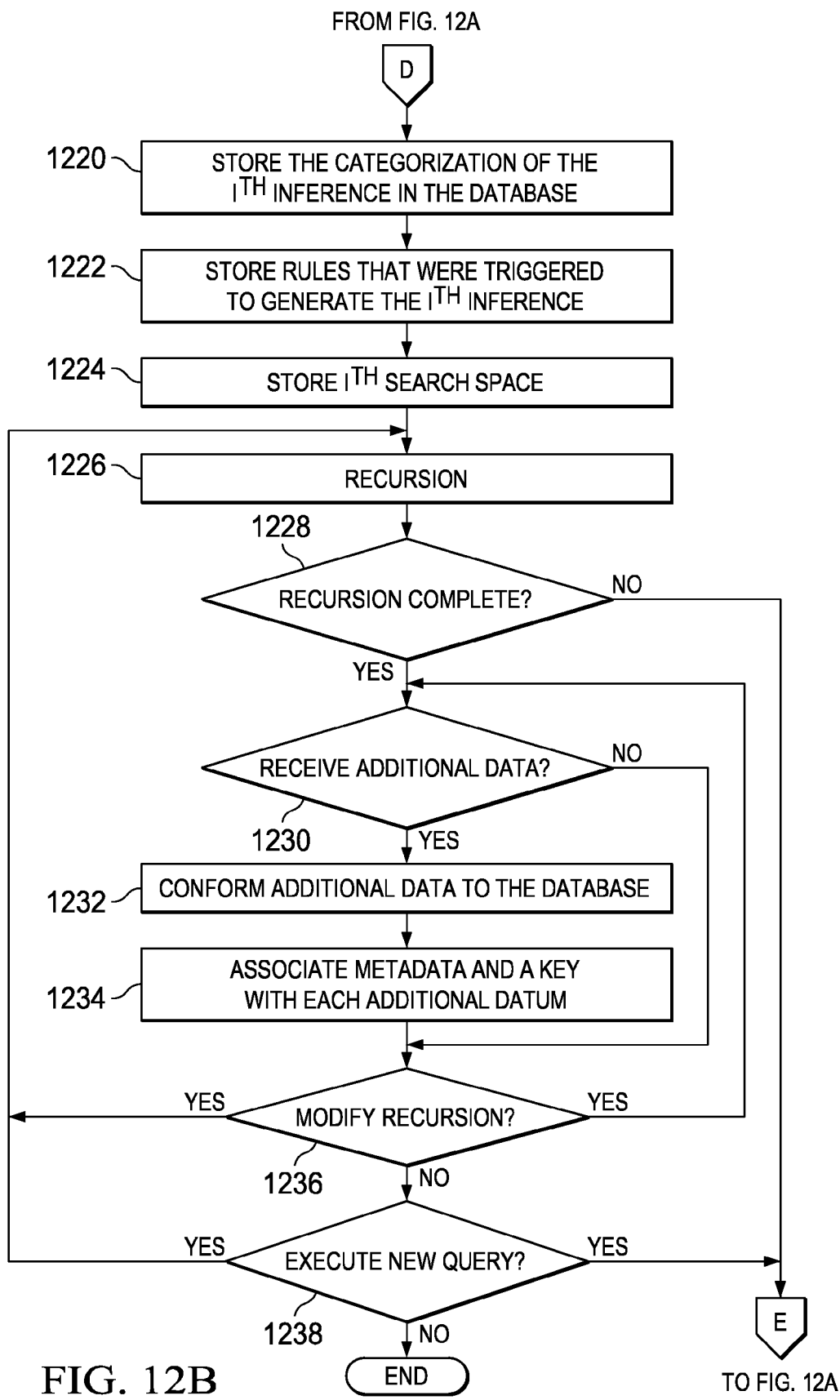

FIGS. 12A and 12B are a flowchart illustrating execution of a query in a database to establish a probability of an inference based on data contained in the database, in accordance with an illustrative embodiment. The process shown in FIGS. 12A and 12B can be implemented using inference engine 1000 and can be implemented in a single data processing system or across multiple data processing systems connected by one or more networks. Whether implemented in a single data processing system or across multiple data processing systems, taken together all data processing systems, hardware, software, and networks are together referred to as a system. The system implements the process.

The process begins as the system receives an $I^{th}$ query regarding an $I^{th}$ fact (step 1200). The term "$I^{th}$" refers to an integer, beginning with one. The integer reflects how many times a recursion process, referred to below, has been conducted. Thus, for example, when a query is first submitted that query is the $1^{st}$ query. The first recursion is the $2^{nd}$ query. The second recursion is the $3^{rd}$ query, and so forth until recursion I-1 forms the "$I^{th}$" query. Similarly, but not the same, the $I^{th}$ fact is the fact associated with the $I^{th}$ query. Thus, the $1^{st}$ fact is associated with the $1^{st}$ query, the $2^{nd}$ fact is associated with the $2^{nd}$ query, etc. The $I^{th}$ fact can be the same as previous facts, such as the $I^{th}$-1 fact, the $I^{th}$-2 fact, etc. The $I^{th}$ fact can be a compound fact. A compound fact is a fact that includes multiple sub-facts. The $I^{th}$ fact can start as a single fact and become a compound fact on subsequent recursions or iterations. The $I^{th}$ fact is likely to become a compound fact during recursion, as additional information is added to the central database during each recursion.

After receiving the $I^{th}$ query, the system establishes the $I^{th}$ fact as a frame of reference for the $I^{th}$ query (step 1202). A frame of reference is an anchor datum or set of data that is used to limit which data are searched in central database 400, that is defines the search space. The frame of reference also is used to determine to what rules the searched data will be subject. Thus, when the query is executed, sufficient processing power will be available to make inferences.

The system then determines an $I^{th}$ set of rules using a $J^{th}$ set of rules (step 1204). In other words, a different set of rules is used to determine the set of rules that are actually applied to the $I^{th}$ query. The term "$J^{th}$" refers to an integer, starting with one, wherein J=1 is the first iteration of the recursion process and I-1 is the $J^{th}$ iteration of the recursion process. The $J^{th}$ set of rules may or may not change from the previous set, such that $J^{th}$-1 set of rules may or may not be the same as the $J^{th}$ set of rules. The term "$J^{th}$" set of rules refers to the set of rules that establishes the search rules, which are the $I^{th}$ set of rules. The $J^{th}$ set of rules is used to determine the $I^{th}$ set of rules.

The system then determines an $I^{th}$ search space (step 1206). The $I^{th}$ search space is the search space for the $I^{th}$ iteration. A search space is the portion of a database, or a subset of data within a database, that is to be searched.

The system then prioritizes the $I^{th}$ set of rules, determined during step 1204, in order to determine which rules of the $I^{th}$ set of rules should be executed first (step 1208). Additionally, the system can prioritize the remaining rules in the $I^{th}$ set of rules. Again, because computing resources are not infinite, those rules that are most likely to produce useful or interesting results are executed first.

After performing steps 1200 through 1206, the system executes the $I^{th}$ query according to the $I^{th}$ set of rules and within the $I^{th}$ search space (step 1210). As a result, the system creates an $I^{th}$ probability of an $I^{th}$ inference (step 1212). As described above, the inference is a conclusion based on a comparison of facts within central database 400. The probability of the inference is the likelihood that the inference is true, or alternatively the probability that the inference is false. The $I^{th}$ probability and the $I^{th}$ inference need not be the same as the previous inference and probability in the recursion process, or one value could change but not the other. For example, as a result of the recursion process the $I^{th}$ inference might be the same as the previous iteration in the recursion process, but the $I^{th}$ probability could increase or decrease over the previous iteration in the recursion process. In contrast, the $I^{th}$ inference can be completely different than the inference created in the previous iteration of the recursion process, with a probability that is either the same or different than the probability generated in the previous iteration of the recursion process.

Next, the system stores the $I^{th}$ probability of the $I^{th}$ inference as an additional datum in central database 400 (step 1214). Similarly, the system stores the $I^{th}$ inference in central database 400 (step 1216), stores a categorization of the probability of the $I^{th}$ inference in central database 400 (step 1218), stores the categorization of the $I^{th}$ inference in the database (step 1220), stores the rules that were triggered in the $I^{th}$ set of rules to generate the $I^{th}$ inference (step 1222), and stores the $I^{th}$ search space (step 1224). Additional information generated as a result of executing the query can also be stored at this time. All of the information stored in steps 1214 through 1224, and possibly in additional storage steps for additional information, can change how the system performs, how the system behaves, and can change the result during each iteration.

The process then follows two paths simultaneously. First, the system performs a recursion process (step 1226) in which steps 1200 through 1224 are continually performed, as described above. Second, the system determines whether additional data is received (step 1230).

Additionally, after each recursion, the system determines whether the recursion is complete (step 1228). The process of recursion is complete when a threshold is met. In one example, a threshold is a probability of an inference. When the probability of an inference decreases below a particular number, the recursion is complete and is made to stop. In another example, a threshold is a number of recursions. Once the given number of recursions is met, the process of recursion stops. Other thresholds can also be used. If the process of recursion is not complete, then recursion continues, beginning again with step 1200.

If the process of recursion is complete, then the process returns to step 1230. Thus, the system determines whether additional data is received at step 1230 during the recursion process in steps 1200 through 1224 and after the recursion process is completed at step 1228. If additional data is received, then the system conforms the additional data to the database (step 1232), as described with respect to FIG. 18. The system also associates metadata and a key with each additional datum (step 1224). A key uniquely identifies an individual datum. A key can be any unique identifier, such as a series of numbers, alphanumeric characters, other characters, or other methods of uniquely identifying objects.

If the system determines that additional data has not been received at step 1230, or after associating metadata and a key with each additional datum in step 1224, then the system determines whether to modify the recursion process (step 1236). Modification of the recursion process can include determining new sets of rules, expanding the search space, performing additional recursions after recursions were completed at step 1228, or continuing the recursion process.

In response to a positive determination to modify the recursion process at step 1236, the system again repeats the determination whether additional data has been received at step 1230 and also performs additional recursions from steps 1200 through 1224, as described with respect to step 1226.

Otherwise, in response to a negative determination to modify the recursion process at step 1236, the system determines whether to execute a new query (step 1238). The system can decide to execute a new query based on an inference derived at step 1212, or can execute a new query based on a prompt or entry by a user. If the system executes a new query, then the system can optionally continue recursion at step 1226, begin a new query recursion process at step 1200, or perform both simultaneously. Thus, multiple query recursion processes can occur at the same time. However, if no new query is to be executed at step 1238, then the process terminates.

Figure 13:
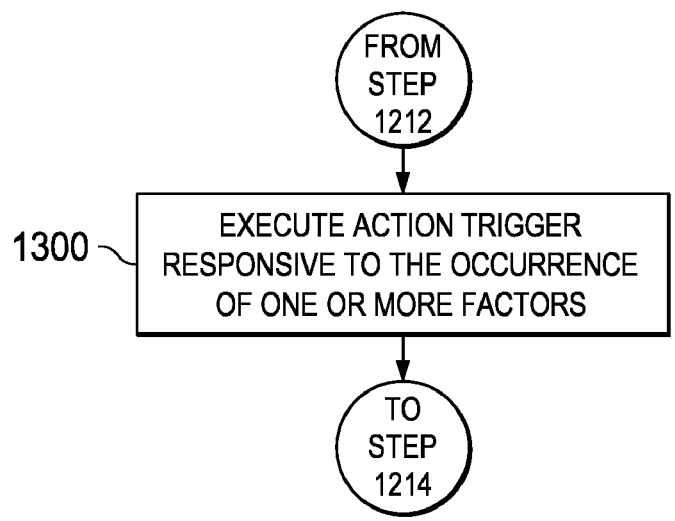
FIG. 13 is a flowchart execution of an action trigger responsive to the occurrence of one or more factors, in accordance with an illustrative embodiment.

FIG. 13 is a flowchart execution of an action trigger responsive to the occurrence of one or more factors, in accordance with an illustrative embodiment. The process shown in FIG. 13 can be implemented using inference engine 1000 and can be implemented in a single data processing system or across multiple data processing systems connected by one or more networks. Whether implemented in a single data processing system or across multiple data processing systems, taken together all data processing systems, hardware, software, and networks are together referred to as a system. The system implements the process.

The exemplary process shown in FIG. 13 is a part of the process shown in FIG. 12. In particular, after step 1212 of FIG. 12, the system executes an action trigger responsive to the occurrence of one or more factors (step 1300). An action trigger is some notification to a user to take a particular action or to investigate a fact or line of research. An action trigger is executed when the action trigger is created in response to a factor being satisfied.

A factor is any established condition. Examples of factors include, but are not limited to, a probability of the first inference exceeding a pre-selected value, a significance of the inference exceeding the same or different pre-selected value, a rate of change in the probability of the first inference exceeding the same or different pre-selected value, an amount of change in the probability of the first inference exceeding the same or different pre-selected value, and combinations thereof.

In one example, a factor is a pre-selected value of a probability. The pre-selected value of the probability is used as a condition for an action trigger. The pre-selected value can be established by a user or by the database, based on rules provided by the database or by the user. The pre-selected probability can be any number between zero percent and one hundred percent.

The exemplary action triggers described herein can be used for scientific research based on inference significance and/or probability. However, action triggers can be used with respect to any line of investigation or inquiry, including medical inquiries, criminal inquiries, historical inquiries, or other inquiries. Thus, action triggers provide for a system for passive information generation can be used to create interventional alerts. Such a system would be particularly useful in the medical research fields.

In a related example, the illustrative embodiments can be used to create an action trigger based on at least one of the biological system and the environmental factor. The action trigger can then be executed based on a parameter associated with at least one of the biological system and the environmental factor. In this example, the parameter can be any associated parameter of the biological system, such as size, complexity, composition, nature, chain of events, or others, and combinations thereof.

Figure 14:
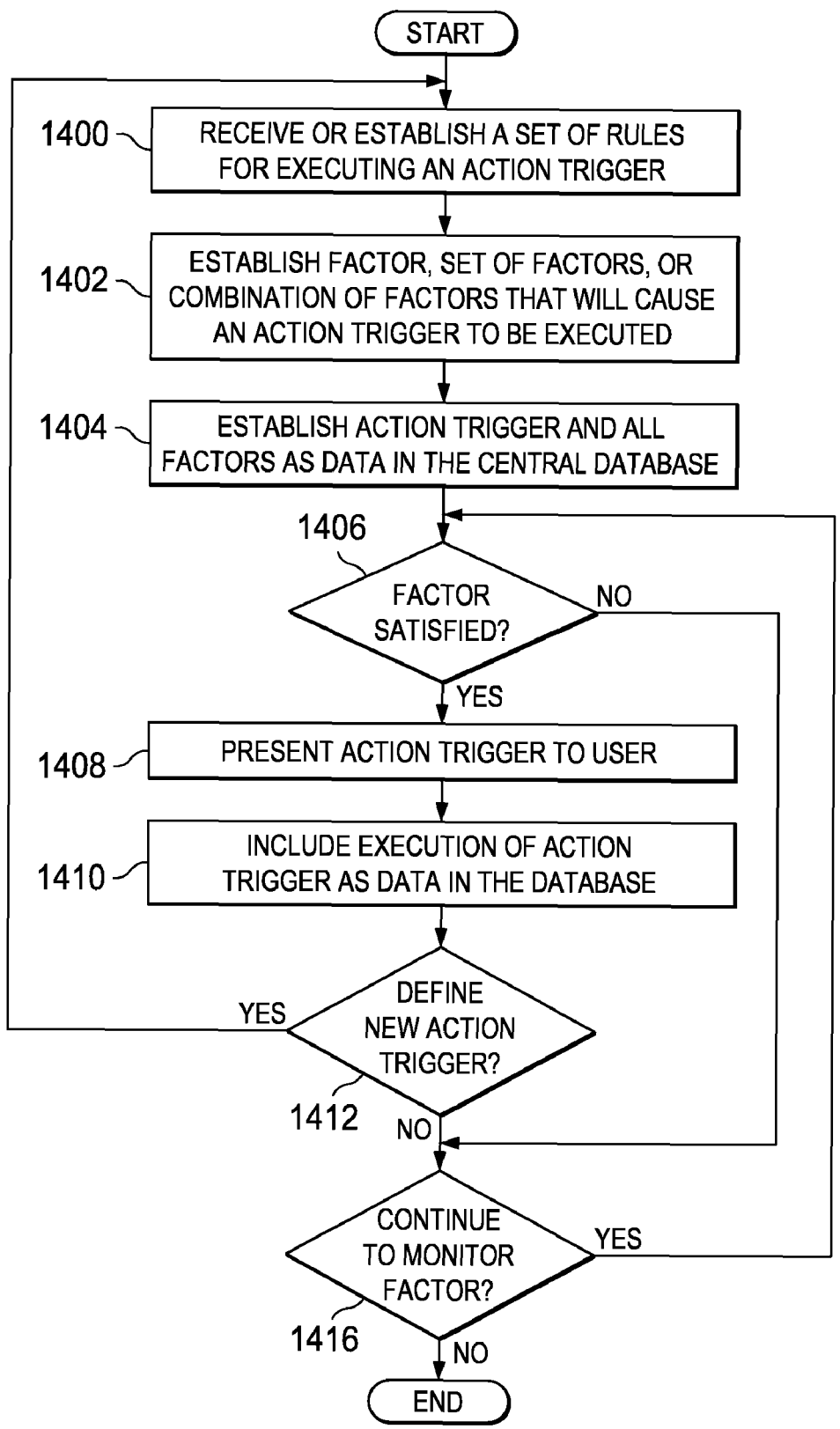
FIG. 14 is a flowchart illustrating an exemplary use of action triggers, in accordance with an illustrative embodiment.

FIG. 14 is a flowchart illustrating an exemplary use of action triggers, in accordance with an illustrative embodiment. The process shown in FIG. 14 can be implemented using inference engine 1000 and can be implemented in a single data processing system or across multiple data processing systems connected by one or more networks. Whether implemented in a single data processing system or across multiple data processing systems, taken together all data processing systems, hardware, software, and networks are together referred to as a system. The system implements the process.

The process shown in FIG. 14 can be a stand-alone process. Additionally, the process shown in FIG. 14 can compose step 1300 of FIG. 13.

The process begins as the system receives or establishes a set of rules for executing an action trigger (step 1400). A user can also perform this step by inputting the set of rules into the database. The system then establishes a factor, a set of factors, or a combination of factors that will cause an action trigger to be executed (step 1402). A user can also perform this step by inputting the set of rules into the database. A factor can be any factor described with respect to FIG. 13. The system then establishes the action trigger and all factors as data in the central database (step 1404). Thus, the action trigger, factors, and all rules associated with the action trigger form part of the central database and can be used when establishing the probability of an inference according to the methods described elsewhere herein.

The system makes a determination whether a factor, set of factors, or combination of factors has been satisfied (step 1406). If the factor, set of factors, or combination of factors has not been satisfied, then the process proceeds to step 1414 for a determination whether continued monitoring should take place. If the factor, set of factors, or combination of factors have been satisfied at step 1406, then the system presents an action trigger to the user (step 1408). An action trigger can be an action trigger as described with respect to FIG. 13.

The system then includes the execution of the action trigger as an additional datum in the database (step 1410). Thus, all aspects of the process described in FIG. 14 are tracked and used as data in the central database.

The system then determines whether to define a new action trigger (step 1412). If a new action trigger is to be defined, then the process returns to step 1400 and the process repeats. However, if a new action trigger is not to be defined at step 1412, or if the factor, set of factors, or combination of factors have not been satisfied at step 1406, then the system determines whether to continue to monitor the factor, set of factors, or combination of factors (step 1414). If monitoring is to continue at step 1414, then the process returns to step 1406 and repeats. If monitoring is not to continue at step 1414, then the process terminates.

The method described with respect to FIG. 14 can be implemented in the form of a number of illustrative embodiments. For example, the action trigger can take the form of a message presented to a user. The message can be a request to a user to analyze one of a probability of the first inference and information related to the probability of the first inference. The message can also be a request to a user to take an action selected from the group including undertaking a particular line of research, investigating a particular fact, and other proposed actions.

In another illustrative embodiment, the action trigger can be an action other than presenting a message or other notification to a user. For example, an action trigger can take the form of one or more additional queries to create one or more probability of one or more additional inferences. In other examples, the action trigger relates to at least one of a security system, an information control system, a biological system, an environmental factor, and combinations thereof.

In another illustrative example, the action trigger is executed based on a parameter associated with one or more of the security system, the information control system, the biological system, and the environmental factor. In a specific illustrative example, the parameter can be one or more of the size, complexity, composition, nature, chain of events, and combinations thereof.

Figure 15:
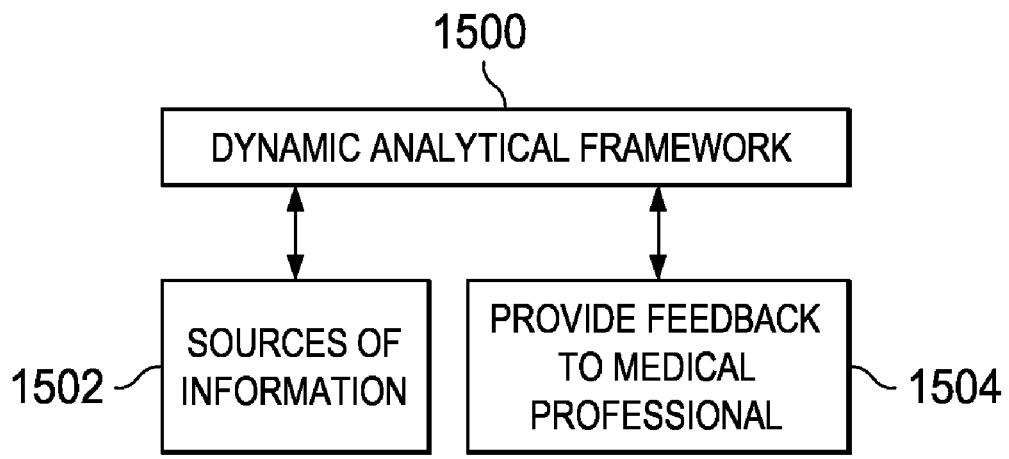
FIG. 15 is a block diagram of a system for providing medical information feedback to medical professionals, in accordance with an illustrative embodiment.

FIG. 15 is a block diagram of a system for providing medical information feedback to medical professionals, in accordance with an illustrative embodiment. The system shown in FIG. 15 can be implemented using one or more data processing systems, including but not limited to computing grids, server computers, client computers, network data processing system 100 in FIG. 1, and one or more data processing systems, such as data processing system 200 shown in FIG. 2. The system shown in FIG. 15 can be implemented using the system shown in FIG. 10. For example, dynamic analytical framework 1500 can be implemented using inference engine 1000 of FIG. 10. Likewise, sources of information 1502 can be any of sources A 1006 through source H 1020 in FIG. 10, or more or different sources. Means for providing feedback to medical professionals 1504 can be any means for communicating or presenting information, including screenshots on displays, emails, computers, personal digital assistants, cell phones, pagers, or one or combinations of multiple data processing systems.

Dynamic analytical framework 1500 receives and/or retrieves data from sources of information 1502. Preferably, each chunk of data is grabbed as soon as a chunk of data is available. Sources of information 1502 can be continuously updated by constantly searching public sources of additional information, such as publications, journal articles, research articles, patents, patent publications, reputable Websites, and possibly many, many additional sources of information. Sources of information 1502 can include data shared through web tool mash-ups or other tools; thus, hospitals and other medical institutions can directly share information and provide such information to sources of information 1502.

Dynamic analytical framework 1500 evaluates (edits and audits), cleanses (converts data format if needed), scores the chunks of data for reasonableness, relates received or retrieved data to existing data, establishes cohorts, performs clustering analysis, performs optimization algorithms, possibly establishes inferences based on queries, and can perform other functions, all on a real-time basis. Some of these functions are described with respect to FIG. 16.

When prompted, or possibly based on some action trigger, dynamic analytical framework 1500 provides feedback to means for providing feedback to medical professionals 1504. Means for providing feedback to medical professionals 1504 can be a screenshot, a report, a print-out, a verbal message, a code, a transmission, a prompt, or any other form of providing feedback useful to a medical professional.

Means for providing feedback to medical professionals 1504 can re-input information back into dynamic analytical framework 1500. Thus, answers and inferences generated by dynamic analytical framework 1500 are re-input back into dynamic analytical framework 1500 and/or sources of information 1502 as additional data that can affect the result of future queries or cause an action trigger to be satisfied. For example, an inference drawn that an epidemic is forming is re-input into dynamic analytical framework 1500, which could cause an action trigger to be satisfied so that professionals at the Center for Disease Control can take emergency action.

Thus, dynamic analytical framework 1500 provides a supporting architecture and a means for providing digesting truly vast amounts of very detailed data and aggregating such data in a manner that is useful to medical professionals. Dynamic analytical framework 1500 provides a method for incorporating the power of set analytics to create highly individualized treatment plans by establishing relationships among data and drawing conclusions based on all relevant data. Dynamic analytical framework 1500 can perform these actions on a real time basis, and further can optimize defined parameters to maximize perceived goals. This process is described more with respect to FIG. 16.

When the illustrative embodiments are implemented across broad medical provider systems, the aggregate results can be dramatic. Not only does patient health improve, but both the cost of health insurance for the patient and the cost of liability insurance for the medical professional are reduced because the associated payouts are reduced. As a result, the real cost of providing medical care, across an entire medical system, can be reduced; or, at a minimum, the rate of cost increase can be minimized.

In an illustrative embodiment, dynamic analytical framework 1500 can be manipulated to access or receive information from only selected ones of sources of information 1502, or to access or receive only selected data types from sources of information 1502. For example, a user can specify that dynamic analytical framework 1500 should not access or receive data from a particular source of information. On the other hand, a user can also specify that dynamic analytical framework 1500 should again access or receive that particular source of information, or should access or receive another source of information. This designation can be made contingent upon some action trigger. For example, should dynamic analytical framework 1500 receive information from a first source of information, dynamic analytical framework 1500 can then automatically begin or discontinue receiving or accessing information from a second source of information. However, the trigger can be any trigger or event.

In a specific example, some medical professionals do not trust, or have lower trust of, patient-reported data. Thus, a medical professional can instruct dynamic analytical framework 1500 to perform an analysis and/or inference without reference to patient-reported data in sources of information 1502. However, to see how the outcome changes with patient-reported data, the medical professional can re-run the analysis and/or inference with the patient-reported data. Continuing this example, the medical professional designates a trigger. The trigger is that, should a particular unlikely outcome arise, then dynamic analytical framework 1500 will discontinue receiving or accessing patient-reported data, discard any analysis performed to that point, and then re-perform the analysis without patient-reported data—all without consulting the medical professional. In this manner, the medical professional can control what information dynamic analytical framework 1500 uses when performing an analysis and/or generating an inference.

In another illustrative embodiment, data from selected ones of sources of information 1502 and/or types of data from sources of information 1502 can be given a certain weight. Dynamic analytical framework 1500 will then perform analyses or generate inferences taking into account the specified weighting.

For example, the medical professional can require dynamic analytical framework 1500 to give patient-related data a low weighting, such as 0.5, indicating that patient-related data should only be weighted 50%. In turn, the medical professional can give DNA tests performed on those patients a higher rating, such as 2.0, indicating that DNA test data should count as doubly weighted. The analysis and/or generated inferences from dynamic analytical framework 1500 can then be generated or re-generated as often as desired until a result is generated that the medical professional deems most appropriate.

This technique can be used to aid a medical professional in deriving a path to a known result. For example, dynamic analytical framework 1500 can be forced to arrive at a particular result, and then generate suggested weightings of sources of data or types of data in sources of information 1502 in order to determine which data or data types are most relevant. In this manner, dynamic analytical framework 1500 can be used to find causes and/or factors in arriving at a known result.

Figure 16:
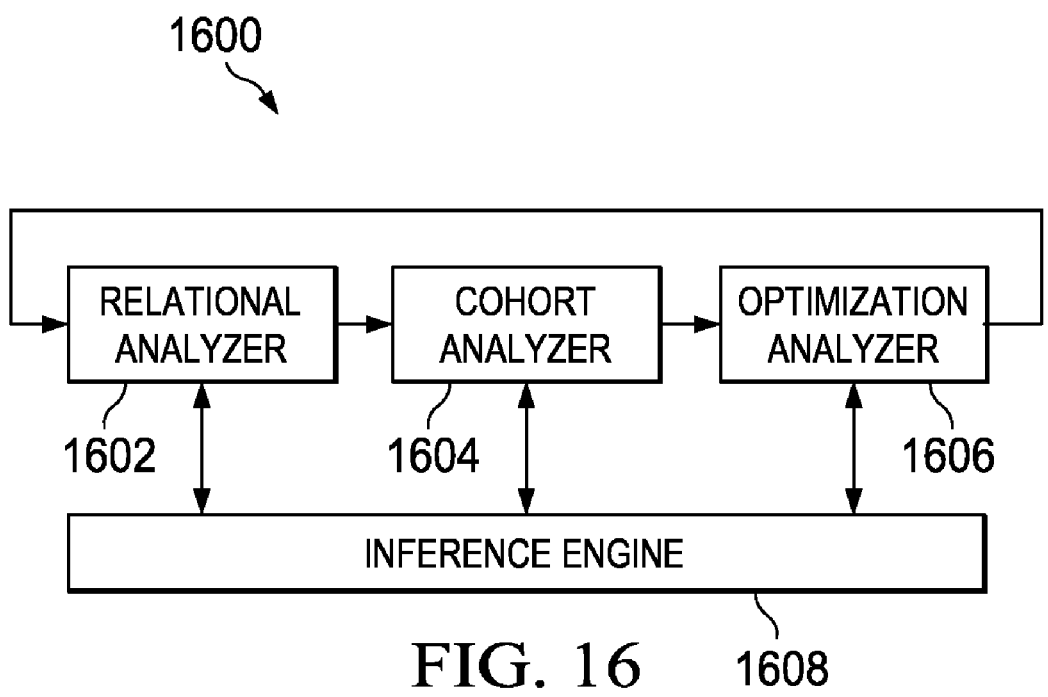
FIG. 16 is a block diagram of a dynamic analytical framework, in accordance with an illustrative embodiment.

FIG. 16 is a block diagram of a dynamic analytical framework, in accordance with an illustrative embodiment. Dynamic analytical framework 1600 is a specific illustrative example of dynamic analytical framework 1500. Dynamic analytical framework 1600 can be implemented using one or more data processing systems, including but not limited to computing grids, server computers, client computers, network data processing system 100 in FIG. 1, and one or more data processing systems, such as data processing system 200 shown in FIG. 2.

Dynamic analytical framework 1600 includes relational analyzer 1602, cohort analyzer 1604, optimization analyzer 1606, and inference engine 1608. Each of these components can be implemented one or more data processing systems, including but not limited to computing grids, server computers, client computers, network data processing system 100 in FIG. 1, and one or more data processing systems, such as data processing system 200 shown in FIG. 2, and can take entirely hardware, entirely software embodiments, or a combination thereof. These components can be performed by the same devices or software programs. These components are described with respect to their functionality, not necessarily with respect to individual identities.

Relational analyzer 1602 establishes connections between received or acquired data and data already existing in sources of information, such as source of information 1502 in FIG. 15. The connections are based on possible relationships amongst the data. For example, patient information in an electronic medical record is related to a particular patient. However, the potential relationships are countless. For example, a particular electronic medical record could contain information that a patient has a particular disease and was treated with a particular treatment. The disease particular disease and the particular treatment are related to the patient and, additionally, the particular disease is related to the particular patient. Generally, electronic medical records, agglomerate patient information in electronic healthcare records, data in a data mart or warehouse, or other forms of information are, as they are received, related to existing data in sources of information 1502, such as source of information 1502 in FIG. 15.

In an illustrative embodiment, using metadata, a given relationship can be assigned additional information that describes the relationship. For example, a relationship can be qualified as to quality. For example, a relationship can be described as "strong," such as in the case of a patient to a disease the patient has, be described as "tenuous," such as in the case of a disease to a treatment of a distantly related disease, or be described according to any pre-defined manner. The quality of a relationship can affect how dynamic analytical framework 1600 clusters information, generates cohorts, and draws inferences.

In another example, a relationship can be qualified as to reliability. For example, research performed by an amateur medical provider may be, for whatever reason, qualified as "unreliable" whereas a conclusion drawn by a researcher at a major university may be qualified as "very reliable." As with quality of a relationship, the reliability of a relationship can affect how dynamic analytical framework 1600 clusters information, generates cohorts, and draws inferences.

Relationships can be qualified along different or additional parameters, or combinations thereof. Examples of such parameters included, but are not limited to "cleanliness" of data (compatibility, integrity, etc.), "reasonability" of data (likelihood of being correct), age of data (recent, obsolete), timeliness of data (whether information related to the subject at issue would require too much time to be useful), or many other parameters.

Established relationships are stored, possibly as metadata associated with a given datum. After establishing these relationships, cohort analyzer 1604 relates patients to cohorts (sets) of patients using clustering, heuristics, or other algorithms. Again, a cohort is a group of individuals, machines, components, or modules identified by a set of one or more common characteristics.

For example, a patient has diabetes. Cohort analyzer 1604 relates the patient in a cohort comprising all patients that also have diabetes. Continuing this example, the patient has type I diabetes and is given insulin as a treatment. Cohort analyzer 1604 relates the patient to at least two additional cohorts, those patients having type I diabetes (a different cohort than all patients having diabetes) and those patients being treated with insulin. Cohort analyzer 1604 also relates information regarding the patient to additional cohorts, such as a cost of insulin (the cost the patient pays is a datum in a cohort of costs paid by all patients using insulin), a cost of medical professionals, side effects experienced by the patient, severity of the disease, and possibly many additional cohorts.

After relating patient information to cohorts, cohort analyzer 1604 clusters different cohorts according to the techniques described with respect to FIG. 3 through FIG. 9. Clustering is performed according to one or more defined parameters, such as treatment, outcome, cost, related diseases, patients with the same disease, and possibly many more. By measuring the Euclidean distance between different cohorts, a determination can be made about the strength of a deduction. For example, by clustering groups of patients having type I diabetes by severity, insulin dose, and outcome, the conclusion that a particular dose of insulin for a particular severity can be assessed to be "strong" or "weak." This conclusion can be drawn by the medical professional based on presented cohort and clustered cohort data, but can also be performed using optimization analyzer 1606.

Optimization analyzer 1606 can perform optimization to maximize one or more parameters against one or more other parameters. For example, optimization analyzer 1606 can use mathematical optimization algorithms to establish a treatment plan with a highest probability of success against a lowest cost. Thus, simultaneously, the quality of healthcare improves, the probability of medical error decreases substantially, and the cost of providing the improved healthcare decreases. Alternatively, if cost is determined to be a lesser factor, then a treatment plan can be derived by performing a mathematical optimization algorithm to determine the highest probability of positive outcome against the lowest probability of negative outcome. In another example, all three of highest probability of positive outcome, lowest probability of negative outcome, and lowest cost can all be compared against each other in order to derive the optimal solution in view of all three parameters.

Continuing the example above, a medical professional desires to minimize costs to a particular patient having type I diabetes. The medical professional knows that the patient should be treated with insulin, but desires to minimize the cost of insulin prescriptions without harming the patient. Optimization analyzer 1606 can perform a mathematical optimization algorithm using the clustered cohorts to compare cost of doses of insulin against recorded benefits to patients with similar severity of type I diabetes at those corresponding doses. The goal of the optimization is to determine at what dose of insulin this particular patient will incur the least cost but gain the most benefit. Using this information, the doctor finds, in this particular case, that the patient can receive less insulin than the doctor's first guess. As a result, the patient pays less for prescriptions of insulin, but receives the needed benefit without endangering the patient.

In another example, the doctor finds that the patient should receive more insulin than the doctor's first guess. As a result, harm to the patient is minimized and the doctor avoided making a medical error using the illustrative embodiments.

Inference engine 1608 can operate with each of relational analyzer 1602, cohort analyzer 1604, and optimization analyzer 1606 to further improve the operation of dynamic analytical framework 1600. Inference engine 1608 is able to generate inferences, not previously known, based on a fact or query. Inference engine 1608 can be inference engine 1000 and can operate according to the methods and devices described with respect to FIG. 10 through FIG. 14.

Inference engine 1608 can be used to improve performance of relational analyzer 1602. New relationships among data can be made as new inferences are made. For example, based on a past query or past generated inference, a correlation is established that a single treatment can benefit two different, unrelated conditions. A specific example of this type of correlation is seen from the history of the drug sildenafil citrate (1-[4-ethoxy-3-(6,7-dihydro-1-methyl-7-oxo-3-propyl-1H-pyrazolo[4,3-d]pyrimidin-5-yl) phenylsulfonyl]-4-methylpiperazine citrate). This drug was commonly used to treat pulmonary arterial hypertension. However, an observation was made that, in some male patients, this drug also improved problems with impotence. As a result, this drug was subsequently marketed as a treatment for impotence. Not only were certain patients with this condition treatment, but the pharmaceutical companies that made this drug were able to profit greatly.

Inference engine 1608 can draw similar inferences by comparing cohorts and clusters of cohorts to draw inferences. Continuing the above example, inference engine 1608 could compare cohorts of patients given the drug sildenafil citrate with cohorts of different outcomes. Inference engine 1608 could draw the inference that those patients treated with sildenafil citrate experienced reduced pulmonary arterial hypertension and also experienced reduced problems with impotence. The correlation gives rise to a probability that sildenafil citrate could be used to treat both conditions. As a result, inference engine 1608 could take two actions: 1) alert a medical professional to the correlation and probability of causation, and 2) establish a new, direct relationship between sildenafil citrate and impotence. This new relationship is stored in relational analyzer 1602, and can subsequently be used by cohort analyzer 1604, optimization analyzer 1606, and inference engine 1608 itself to draw new conclusions and inferences.

Similarly, inference engine 1608 can be used to improve the performance of cohort analyzer 1604. Based on queries, facts, or past inferences, new inferences can be made regarding relationships amongst cohorts. Additionally, new inferences can be made that certain objects should be added to particular cohorts. Continuing the above example, sildenafil citrate could be added to the cohort of "treatments for impotence." The relationship between the cohort "treatments for impotence" and the cohort "patients having impotence" is likewise changed by the inference that sildenafil citrate can be used to treat impotence.

Similarly, inference engine 1608 can be used to improve the performance of optimization analyzer 1606. Inferences drawn by inference engine 1608 can change the result of an optimization process based on new information. For example, in an hypothetically speaking only, had sildenafil citrate been a less expensive treatment for impotence than previously known treatments, then this fact would be taken into account by optimization analyzer 1606 in considering the best treatment option at lowest cost for a patient having impotence.

Still further, inferences generated by inference engine 1608 can be presented, by themselves, to medical professionals through, for example, means for providing feedback to medical professionals 1504 of FIG. 15. In this manner, attention can be drawn to a medical professional of new, possible treatment options for patients. Similarly, attention can be drawn to possible causes for medical conditions that were not previously considered by the medical professional. Such inferences can be ranked, changed, and annotated by the medical professional. Such inferences, including any annotations, are themselves stored in sources of information 1502. The process of data acquisition, query, relationship building, cohort building, cohort clustering, optimization, and inference can be repeated multiple times as desired to achieve a best possible inference or result. In this sense, dynamic analytical framework 1600 is capable of learning.

The illustrative embodiments can be further improved. For example, sources of information 1502 can include the details of a patient's insurance plan. As a result, optimization analyzer 1606 can maximize a cost/benefit treatment option for a particular patient according to the terms of that particular patient's insurance plan. Additionally, real-time negotiation can be performed between the patient's insurance provider and the medical provider to determine what benefit to provide to the patient for a particular condition.

Sources of information 1502 can also include details regarding a patient's lifestyle. For example, the fact that a patient exercises rigorously once a day can influence what treatment options are available to that patient.

Sources of information 1502 can take into account available medical resources at a local level or at a remote level. For example, treatment rankings can reflect locally available therapeutics versus specialized, remotely available therapeutics.

Sources of information 1502 can include data reflecting how time sensitive a situation or treatment is. Thus, for example, dynamic analytical framework 1500 will not recommend calling in a remote trauma surgeon to perform cardiopulmonary resuscitation when the patient requires emergency care.

Still further, information generated by dynamic analytical framework 1600 can be used to generate information for financial derivatives. These financial derivatives can be traded based on an overall cost to treat a group of patients having a certain condition, the overall cost to treat a particular patient, or many other possible derivatives.

In another illustrative example, the illustrative embodiments can be used to minimize false positives and false negatives. For, example, if a parameter along which cohorts are clustered are medical diagnoses, then parameters to optimize could be false positives versus false negatives. In other words, when the at least one parameter along which cohorts are clustered comprises a medical diagnosis, the second parameter can comprise false positive diagnoses, and the third parameter can comprise false negative diagnoses. Clusters of cohorts having those properties can then be analyzed further to determine which techniques are least likely to lead to false positives and false negatives.

When the illustrative embodiments are implemented across broad medical provider systems, the aggregate results can be dramatic. Not only does patient health improve, but both the cost of health insurance for the patient and the cost of liability insurance for the medical professional are reduced because the associated payouts are reduced. As a result, the real cost of providing medical care, across an entire medical system, can be reduced; or, at a minimum, the rate of cost increase can be minimized.

Figure 17:
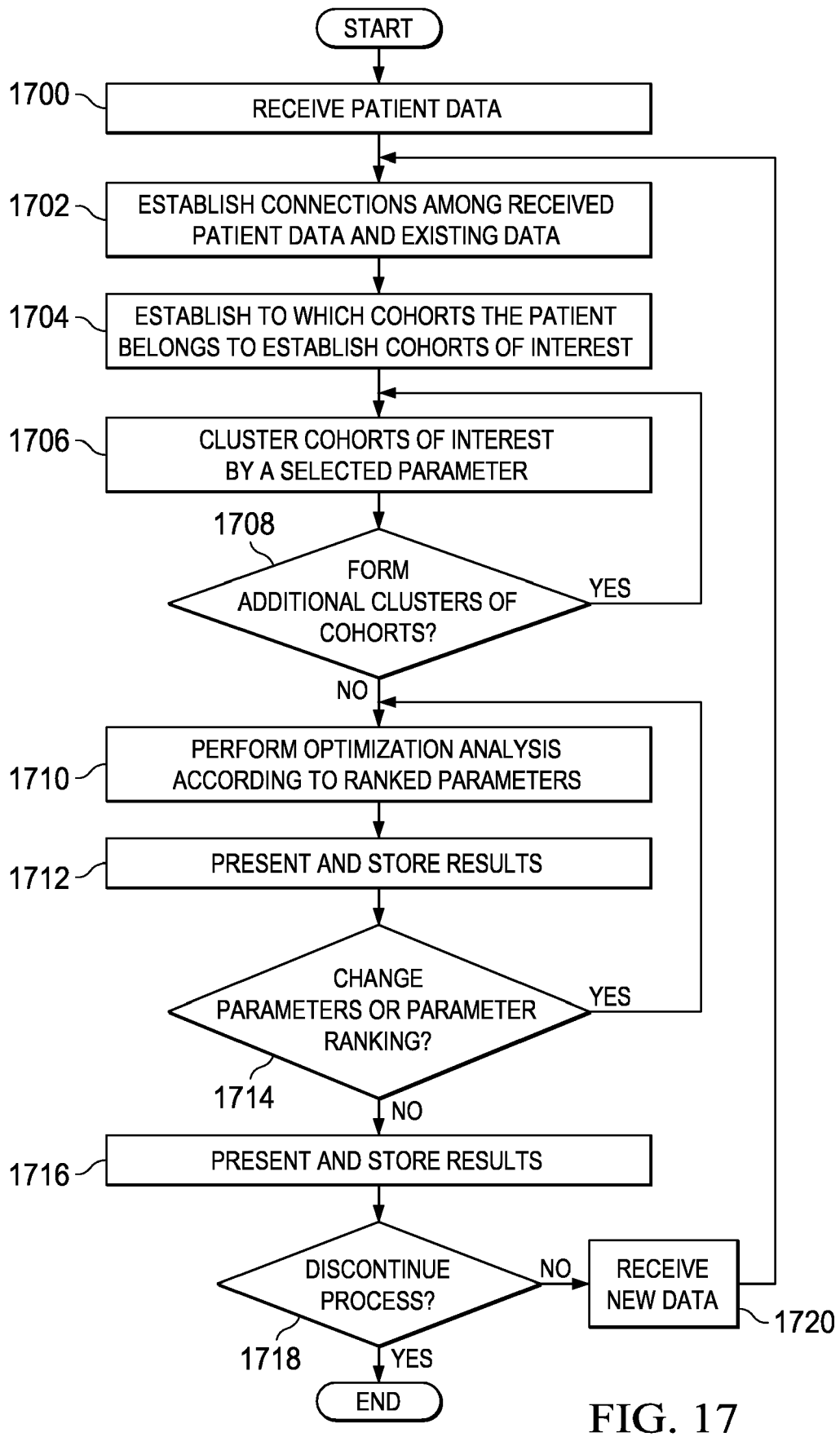
FIG. 17 is a flowchart of a process for presenting medical information feedback to medical professionals, in accordance with an illustrative embodiment.

FIG. 17 is a flowchart of a process for presenting medical information feedback to medical professionals, in accordance with an illustrative embodiment. The process shown in FIG. 17 can be implemented using dynamic analytical framework 1500 in FIG. 15, dynamic analytical framework 1600 in FIG. 16, and possibly include the use of inference engine 1000 shown in FIG. 10. Thus, the process shown in FIG. 17 can be implemented using one or more data processing systems, including but not limited to computing grids, server computers, client computers, network data processing system 100 in FIG. 1, and one or more data processing systems, such as data processing system 200 shown in FIG. 2, and other devices as described with respect to FIG. 1 through FIG. 16. Together, devices and software for implementing the process shown in FIG. 17 can be referred-to as a "system."

The process begins as the system receives patient data (step 1700). The system establishes connections among received patient data and existing data (step 1702). The system then establishes to which cohorts the patient belongs in order to establish "cohorts of interest" (step 1704). The system then clusters cohorts of interest according to a selected parameter (step 1706). The selected parameter can be any parameter described with respect to FIG. 16, such as but not limited to treatments, treatment effectiveness, patient characteristics, and medical conditions.

The system then determines whether to form additional clusters of cohorts (step 1708). If additional clusters of cohorts are to be formed, then the process returns to step 1706 and repeats.

Additional clusters of cohorts are not to be formed, then the system performs optimization analysis according to ranked parameters (step 1710). The ranked parameters include those parameters described with respect to FIG. 16, and include but are not limited to maximum likely benefit, minimum likely harm, and minimum cost. The system then both presents and stores the results (step 1712).

The system then determines whether to change parameters or parameter rankings (step 1714). A positive determination can be prompted by a medical professional user. For example, a medical professional may reject a result based on his or her professional opinion. A positive determination can also be prompted as a result of not achieving an answer that meets certain criteria or threshold previously input into the system. In any case, if a change in parameters or parameter rankings is to be made, then the system returns to step 1710 and repeats. Otherwise, the system presents and stores the results (step 1716).

The system then determines whether to discontinue the process. A positive determination in this regard can be made in response to medical professional user input that a satisfactory result has been achieved, or that no further processing will achieve a satisfactory result. A positive determination in this regard could also be made in response to a timeout condition, a technical problem in the system, or to a predetermined criteria or threshold.

In any case, if the system is to continue the process, then the system receives new data (step 1720). New data can include the results previously stored in step 1716. New data can include data newly acquired from other databases, such as any of the information sources described with respect to sources of information 1502 of FIG. 15, or data input by a medical professional user that is specifically related to the process at hand. The process then returns to step 1702 and repeats. However, if the process is to be discontinued at step 1718, then the process terminates.

Figure 18:
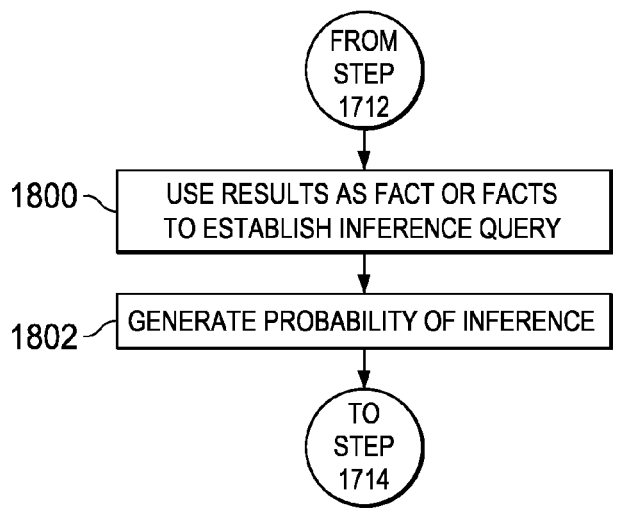
FIG. 18 is a flowchart of a process for presenting medical information feedback to medical professionals, in accordance with an illustrative embodiment.

FIG. 18 is a flowchart of a process for presenting medical information feedback to medical professionals, in accordance with an illustrative embodiment. The process shown in FIG. 18 is a particular example of using clustering set analytics together with an inference engine, such as inference engine 1000 in FIG. 10. The process shown in FIG. 18 can be implemented using dynamic analytical framework 1500 in FIG. 15, dynamic analytical framework 1600 in FIG. 16, and possibly include the use of inference engine 1000 shown in FIG. 10. Thus, the process shown in FIG. 18 can be implemented using one or more data processing systems, including but not limited to computing grids, server computers, client computers, network data processing system 100 in FIG. 1, and one or more data processing systems, such as data processing system 200 shown in FIG. 2, and other devices as described with respect to FIG. 1 through FIG. 16. Together, devices and software for implementing the process shown in FIG. 18 can be referred-to as a "system."

The process shown in FIG. 18 is an extension of the process described with respect to FIG. 17. Thus, from step 1712 of FIG. 17, the system uses the stored results as a fact or facts to establish a frame of references for a query (step 1800). Based on this query, the system generates a probability of an inference (step 1802). The process of generating a probability of an inference, and examples thereof, are described with respect to FIG. 16 and FIGS. 12A and 12B. The process then proceeds to step 1714 of FIG. 17.

Figure 19:
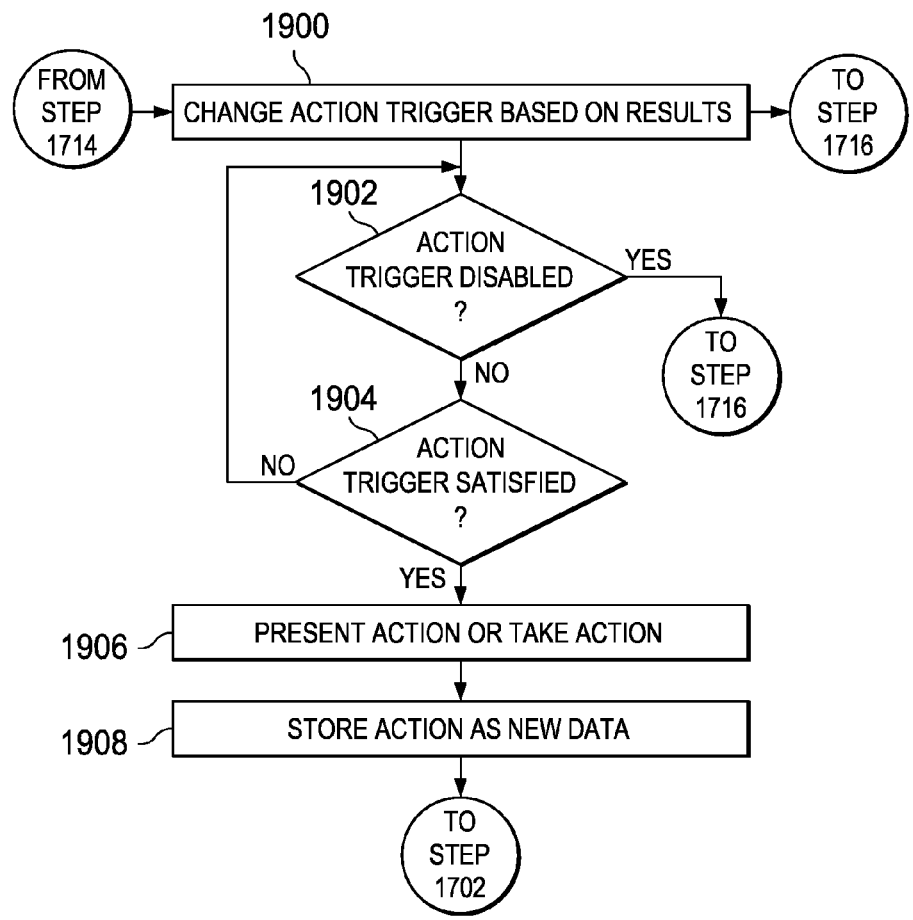
FIG. 19 is a flowchart of a process for presenting medical information feedback to medical professionals, in accordance with an illustrative embodiment.

FIG. 19 is a flowchart of a process for presenting medical information feedback to medical professionals, in accordance with an illustrative embodiment. The process shown in FIG. 19 is a particular example of using clustering set analytics together with action triggers, as described in FIG. 14. The process shown in FIG. 19 can also incorporate the use of an inference engine, as described with respect to FIG. 18. The process shown in FIG. 19 can be implemented using dynamic analytical framework 1500 in FIG. 15, dynamic analytical framework 1600 in FIG. 16, and possibly include the use of inference engine 1000 shown in FIG. 10. Thus, the process shown in FIG. 19 can be implemented using one or more data processing systems, including but not limited to computing grids, server computers, client computers, network data processing system 100 in FIG. 1, and one or more data processing systems, such as data processing system 200 shown in FIG. 2, and other devices as described with respect to FIG. 1 through FIG. 16. Together, devices and software for implementing the process shown in FIG. 19 can be referred-to as a "system."

The process shown in FIG. 19 is an extension of the process shown in FIG. 17. Thus, from step 1714 of FIG. 17, the system changes an action trigger based on the stored results (step 1900). The system then both proceeds to step 1716 of FIG. 17 and also determines whether the action trigger should be disabled (step 1902).

If the action trigger is to be disabled, then the action trigger is disabled and the process returns to step 1716. If not, then the system determines whether the action trigger has been satisfied (step 1904). If the action trigger has not been satisfied, then the process returns to step 1902 and repeats.

However, if the action trigger is satisfied, then the system presents the action or takes an action, as appropriate (step 1906). For example, the system, by itself, can take the action of issuing a notification to a particular user or set of users. In another example, the system presents information to a medical professional or reminds the medical professional to take an action.

The system then stores the action, or lack thereof, as new data in sources of information 1502 (step 1908). The process then returns to step 1702 of FIG. 17.

Figure 20:
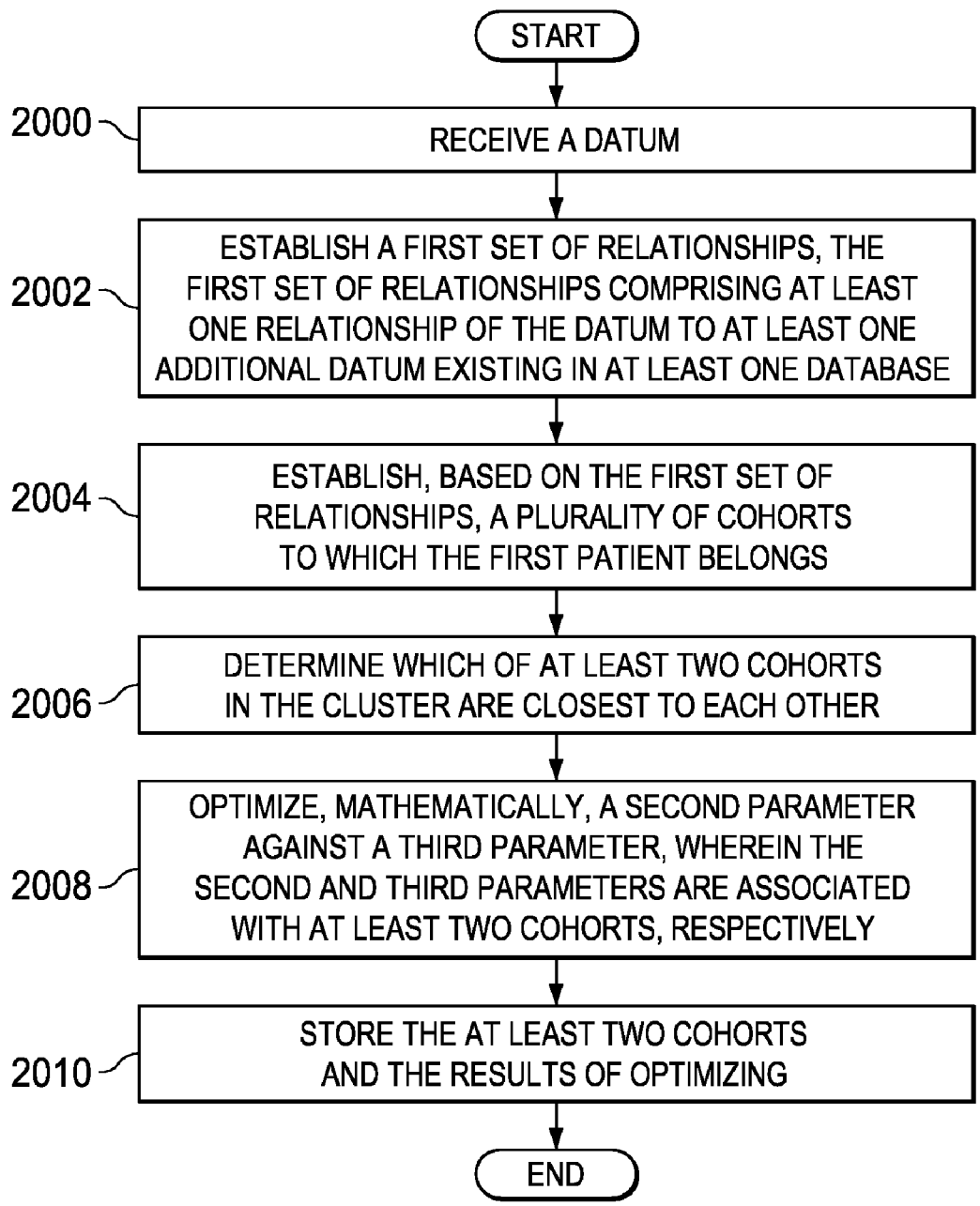
FIG. 20 is a flowchart of a process for presenting medical information feedback to medical professionals, in accordance with an illustrative embodiment.

FIG. 20 is a flowchart of a process for presenting medical information feedback to medical professionals, in accordance with an illustrative embodiment. The process shown in FIG. 19 can be implemented using dynamic analytical framework 1500 in FIG. 15, dynamic analytical framework 1600 in FIG. 16, and possibly include the use of inference engine 1000 shown in FIG. 10. Thus, the process shown in FIG. 20 can be implemented using one or more data processing systems, including but not limited to computing grids, server computers, client computers, network data processing system 100 in FIG. 1, and one or more data processing systems, such as data processing system 200 shown in FIG. 2, and other devices as described with respect to FIG. 1 through FIG. 16. Together, devices and software for implementing the process shown in FIG. 20 can be referred-to as a "system."

The process begins as a datum regarding a first patient is received (step 2000). The datum can be received by transmission to the system, or by the actively retrieving the datum. A first set of relationships is established, the first set of relationships comprising at least one relationship of the datum to at least one additional datum existing in at least one database (step 2002). A plurality of cohorts to which the first patient belongs is established based on the first set of relationships (step 2004). Ones of the plurality of cohorts contain corresponding first data regarding the first patient and corresponding second data regarding a corresponding set of additional information. The corresponding set of additional information is related to the corresponding first data. The plurality of cohorts is clustered according to at least one parameter, wherein a cluster of cohorts is formed. A determination is made of which of at least two cohorts in the cluster are closest to each other (step 2006). The at least two cohorts can be stored.

In another illustrative embodiment, a second parameter is optimized, mathematically, against a third parameter (step 2008). The second parameter is associated with a first one of the at least two cohorts. The third parameter is associated with a second one of the at least two cohorts. A result of optimizing can be stored, along with (optionally) the at least two cohorts (step 2010). The process terminates thereafter.

In another illustrative embodiment, establishing the plurality of cohorts further comprises establishing to what degree a patient belongs in the plurality of cohorts. In yet another illustrative embodiment the second parameter comprises treatments having a highest probability of success for the patient and the third parameter comprises corresponding costs of the treatments.

In another illustrative embodiment, the second parameter comprises treatments having a lowest probability of negative outcome and the second parameter comprises a highest probability of positive outcome. In yet another illustrative embodiment, the at least one parameter comprises a medical diagnosis, wherein the second parameter comprises false positive diagnoses, and wherein the third parameter comprises false negative diagnoses.

When the illustrative embodiments are implemented across broad medical provider systems, the aggregate results can be dramatic. Not only does patient health improve, but both the cost of health insurance for the patient and the cost of liability insurance for the medical professional are reduced because the associated payouts are reduced. As a result, the real cost of providing medical care, across an entire medical system, can be reduced; or, at a minimum, the rate of cost increase can be minimized.

Figure 21:
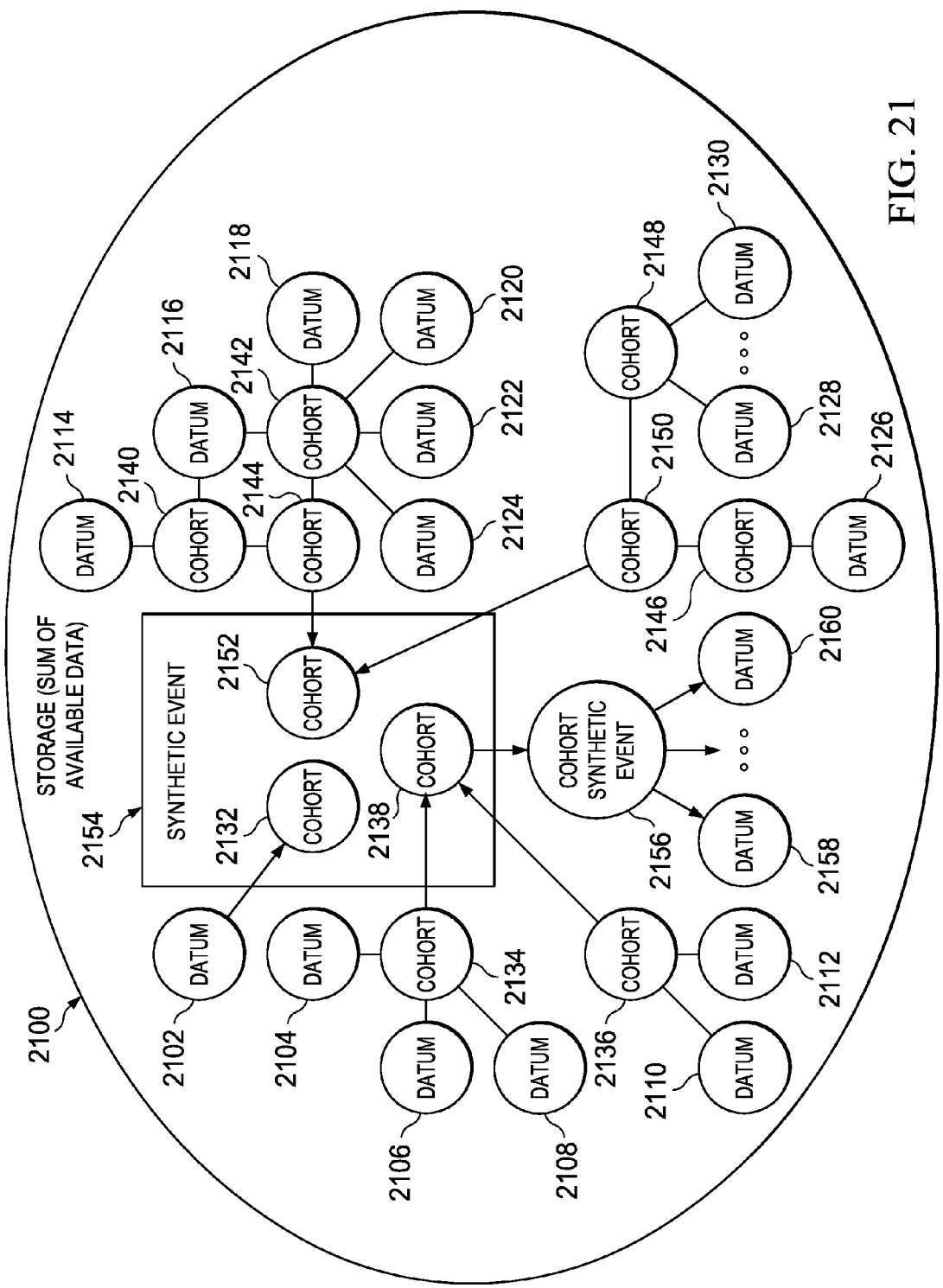
FIG. 21 is a block diagram illustrating combinations of cohorts to generate a synthetic event, in accordance with an illustrative embodiment.

FIG. 21 is a block diagram illustrating combinations of cohorts to generate a synthetic event, in accordance with an illustrative embodiment. Each cohort shown in FIG. 21 can be generated and stored according to the techniques described with respect to FIG. 3 through FIG. 9. The synthetic event shown in FIG. 21 can be calculated using the inference engine and the techniques described with respect to FIG. 10 through FIG. 20. Thus, the process shown in FIG. 21 can be implemented using one or more data processing systems, including but not limited to computing grids, server computers, client computers, network data processing system 100 in FIG. 1, and one or more data processing systems, such as data processing system 200 shown in FIG. 2, and other devices as described with respect to FIG. 1 through FIG. 16. Together, devices and software for implementing the process shown in FIG. 20 can be referred-to as a "system."

Before describing combinations of cohorts to generate a synthetic event, several terms are defined. The term "datum" is defined as a single fact represented in a mathematical manner, usually as a binary number. A datum could be one or more bytes. A datum may have associated with it metadata, as described with respect to FIG. 3 through FIG. 20.

The term "cohort" is defined as data that represents a group of individuals, machines, components, or modules identified by a set of one or more common characteristics. A cohort may have associated with it metadata, as described with respect to FIG. 3 through FIG. 20.

An "event" is defined as a particular set of data that represents, encodes, or records at least one of a thing or happening. A happening is some occurrence defined in time, such as but not limited to the fact that a certain boat passed a certain buoy at a certain time. Thus, the term "event" is not used according to its ordinary and customary English meaning.

Events can be processed by computers by processing objects that represent the events. An event object is a set of data arranged into a data structure, such as a vector, row, cube, or some other data structure. A given activity may be represented by more than one event object. Each event object might record different attributes of the activity. Non-limiting examples of "events" include purchase orders, email confirmation of an airline reservation, a stock tick message that reports a stock trade, a message that reports an RFID sensor reading, a medical insurance claim, a healthcare record of a patient, a video recording of a crime, and many, many other examples.

A complex event is defined as an abstraction of other events which are members of the complex event. A complex event can be a cohort, though a cohort need not be a complex event. Examples of complex events include the 1929 stock market crash (an abstraction denoting many thousands of member events, including individual stock trades), a CPU instruction (an abstraction of register transfer level events), a completed stock purchase (an abstraction of the events in a transaction to purchase the stock), a successful on-line shopping cart checkout (an abstraction of shopping cart events on an on-line website), and a school transcript (an abstraction of a record of classes taken by a particular student). Many, many other examples of complex events exist.

A "synthetic event" is defined as an "event" that represents a probability of a future fact or happening, or that represents a probability that a potential past fact or happening has occurred, or that represents a probability that a potential current fact or happening is occurring, with the mathematical formulation of a synthetic event represented by the operation $S(p1) \Longrightarrow F(p2)$, where S is the set of input facts with probability p1 that potentiates future event F with probability p2. Note that future event F in this operation can represent represents a probability that a potential past fact or happening has occurred, or that represents a probability that a potential current fact or happening is occurring, because these probabilities did not exist before a request to calculate them was formulated. Additionally, a synthetic event can be considered a recordable, definable, addressable data interrelationship in solution space, wherein the interrelationship is represented with a surrogate key, and wherein the synthetic event is able to interact with other events or facts for purposes of computer-assisted analysis.

Synthetic events are composed of physically or logically observable events, not suppositions about mental state, unless they can be supported by or characterized as observable fact or numbers. Synthetic events can be compared to generate additional synthetic evens. For example, a previously derived synthetic event is a conclusion that business "B" appears to be entering a market area with probability p1. A second previously derived synthetic event is that, within probability p2, an unknown company is engaging in a large scale hiring of personnel with skill necessary to compete with a particular product line. These two synthetic events can be compared and processed to derive a probability, p3, that business "B" intends to enter into business competition with the particular product line. Other events or synthetic events could be added or combined to the first two previous synthetic events to modify the probability p3.

Returning to FIG. 21, the improved genesis of synthetic events is described. Storage 2100 represents one or more storage units, including RAM, ROM, hard drives, flash disks, or any other form of memory. Storage 2100 contains the sum of data available for processing. As described above, data is preferably stored at the atomic level, meaning that each individual datum is addressable and recordable and has associated with it metadata that allows meaningful manipulation of the data. Any given amount of data can exist within storage 2100, though in this example storage 2100 includes datum 2102, datum 2104, datum 2106, datum 2108, datum 2110, datum 2112, datum 2114, datum 2116, datum 2118, datum 2120, datum 2122, datum 2124, datum 2126, datum 2128, and datum 2130, which are all present before the creation of a synthetic event.

A cohort analyzer, such as cohort analyzer 1604 of FIG. 16, can group these data into cohorts. A cohort can comprise a single datum, such as for example in the case of cohort 2132, which includes datum 2102. Cohort 2132 is different from datum 2102 in that cohort 2132 includes additional data that makes it a potential grouping if at least one additional datum is included in cohort 2132. For example, only a single patient in a study is known to be infected with a virus type that causes acquired immune deficiency syndrome (AIDS). However, a researcher or a computer program can establish a cohort that includes "the set of all patients in the study that have the virus type that causes AIDS." For the moment, cohort 2132 includes only one member, but additional members could be added. Thus, cohort 2132 is different than datum 2102 alone.

As implied above, multiple datums (data) can be represented as a single cohort. Thus, for example, datum 2104, datum 2106, and datum 2108 together are part of cohort 2134. Likewise, datum 2110 and 2112 together are part of cohort 2136. Similarly, datum 2114 and datum 2116 together are part of cohort 2140; and datum 2118, datum 2120, datum 2122, and datum 2124 together are part of cohort 2142. A cohort, such as cohort 2148 can include a vast plurality of data, as represented by the ellipsis between datum 2128 and datum 2130. Finally, datum 2126 is part of cohort 2146.

To add additional levels of abstraction, cohorts can themselves be combined into broader cohorts. For example, cohort 2134 is combined with cohort 2136 to form cohort 2138. As a specific example, cohort 2138 could be "cancer," with cohort 2134 representing incidents of colon cancer and cohort 2136 representing incidents of pancreatic cancer.

Many levels of cohorts and abstraction are possible. For example, cohort 2140 and cohort 2142 combine to form cohort 2144. Cohort 2146 and cohort 2148 combine to form cohort 2150. Thereafter, cohort 2144 and cohort 2150 are themselves combined to form cohort 2152.

Each cohort is considered an "event." Each cohort, or event, is represented as a pointer which points back to the individual members of the cohort; in other words, each cohort is represented as a pointer which points back to each cohort, datum, or other event that forms the cohort. As a result, a single cohort can be processed as a single pointer, even if the pointer points to billions of subcomponents. Each pointer is fully addressable in a computer; thus, each cohort or other event is fully addressable in a computer.

Because each cohort can be processed as a single pointer, even cohorts having billions, trillions, or more members can be processed as a single pointer. For this reason, computationally explosive computations become manageable.

In the illustrative embodiment of FIG. 21, cohort 2132, cohort 2138, and cohort 2152 are to be analyzed to generate synthetic event 2154. An example of an analysis is inference analysis, as described with respect to FIG. 10 through FIG. 20. An example of an analysis is the generation of generate synthetic event 2154 according to the formula S(p1)==>F (p2), as further described above.

As a result of the generation of generate synthetic event 2154, cohort 2156 is formed. In an illustrative embodiment, cohort 2156 is the synthetic event. However, generate synthetic event 2154 could be composed of multiple cohorts, of which cohort 2156 is a member. Thus, cohort 2156 is a result of the analysis performed on the group comprising cohort 2132, cohort 2138, and cohort 2152.

Cohort 2156 itself is a pointer that refers to sub-members or sub-components related to the analysis. The sub-members of cohort 2156 are derived from the members of cohort 2132, cohort 2138, and cohort 2152. Thus, cohort 2156 can be conceivably composed of a vast plurality of sub-members. In this case, cohort 2156 includes datum 2158 through datum 2160, together with many data represented by the ellipsis. Preferably, not all of the sub-members of cohort 2132, cohort 2138, and cohort 2152 are also sub-members of cohort 2156. Part of the effort of the analysis that generates generate synthetic event 2154 is to narrow the realm of relevant data in order to render computationally explosive calculations amenable to numerical solutions.

Additionally, cohort 2156 can itself be a pointer that points to other cohorts. Thus, for example, cohort 2156 could have a pointer structure similar to the pointer structure that forms cohort 2152.

Because each event or cohort is represented as a pointer, extremely specific information can be obtained. For example, cohort 2132 represents a genetic sequence of a particular patient, cohort 2138 represents a pool of genetic sequences, and cohort 2152 represents diet habits of a particular ethnic group. An inference analysis is performed with the goal of determining a probability that the particular patient will develop a form of cancer in his or her lifetime. In this illustrative embodiment, cohort 2156 could be the group of individuals that are likely to develop cancer, with datum 2158 representing the individual patient in question. Thus, a doctor, researcher, or analyst can "drill down" to achieve reliable conclusions regarding specific items or individuals based on an analysis of a truly vast body of data.

The illustrative embodiments can be described by way of a specific, non-limiting example of a problem to be solved and the implemented solution. The following examples are only provided as an aid to understanding the illustrative embodiments, not to limiting them.

A group of medical researchers are interested in determining if an ethnic diet interacts with genetic background to increase incidents of heart attacks. First, data is collected regarding individual persons who report eating specific ethnic foods to create an "ethnic food" event. The ethnic food events includes items such as chicken fried steak, ribs, pizza with cheese and meat toppings, deep fat fried cheese sticks, and fried candy bars. Additional data is collected from medical literature to find documented clusters of genes indicative of specific geographic origins. These clusters of gene patterns are used to define "geographic gene cluster" events. For example, information can be obtained from the IBM/National Geographic Worldwide Geographic Project to determine indicative clusters. Individual persons are assigned to specific clusters, such as Asian-Chinese, Asian-Japanese, European-Arctic Circle, European-Mediterranean, and others.

Next, individual persons are assigned to "Ultraviolet Light (UV) exposure" events, or cohorts, using individual personal logs and the typical UV exposures for their location of residence. This information is used to create synthetic events called "UV exposure events," which will measure and rank probable severity of exposure for each individual.

Next, data is obtained about drugs that are currently known to affect heart frequency. Data is also obtained regarding the drug usage history of individual persons using personal logs, insurance payments for drugs, recorded prescriptions for drugs, or personally reported information. Individual persons are then identified with synthetic drug events, such as "analgesic-aspirin," "analgesic-generic," "statins-LIPITOR®", statins-ZOCOR®," "statins-generic," and "statins-unknown." The "statin" events, or cohorts, are then adjusted to be equivalent to a LIPITOR® equivalent dosage, which would itself compose a "LIPITOR® equivalent" event, or cohort. At this point, these drugs can be analyzed at a generic, name specific, or equivalent dosage level of detail.

Next, persons in the study group that have died are identified, with the cause of death determined from retrieved death certificates. If the cause of death is "heart related," then those deceased persons would be added to a user-generated synthetic event called "cardio mortalities." All other deaths are assigned to a user-generated synthetic event called "non-cardio mortalities." All other participants would be assigned to a third user-generated event called "living participants."

At this point, a statistical analysis is performed to accept or reject the null hypothesis that consumption of the defined ethnic foods has no effect on the "cardio mortalities" synthetic event. The result is, itself, a computer-generated synthetic event, or cohort. Assume that the null hypothesis is false; in other words, that the consumption of the defined ethnic foods does have an effect on the cardio mortalities synthetic event. In this case, the generated synthetic event can be analyzed in further detail to glean additional detail regarding not only a probability of the truth of the converse positive hypothesis (that the ethnic foods do cause heart-related deaths), but also to determine why those foods cause the heart attacks based on genetic factors.

As more synthetic events are generated, user feedback provided, and as additional raw data become available, the analysis process can be iterated many times until a reliable and accurate answer is achieved. As a result, a truly vast amount of data can be analyzed to find conclusions and reasons for why the conclusions are true or false. The conclusions can be extremely specific, even down to the individual patient level.

Figure 22:
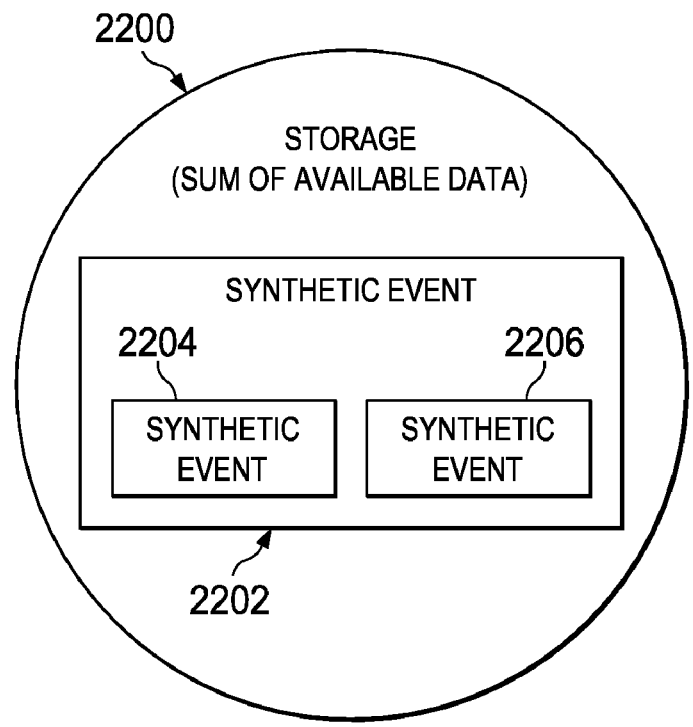
FIG. 22 is a block diagram illustrating a combination of synthetic events, in accordance with an illustrative embodiment.

FIG. 22 is a block diagram illustrating a combination of synthetic events, in accordance with an illustrative embodiment. The synthetic events shown in FIG. 22 are calculated in a manner similar to that presented with respect to FIG. 21. Storage 2200 is similar to storage 2100 in FIG. 21, which represents the storage devices that contain the sum of available data.

FIG. 22 shows that additional synthetic events can be generated by combining other synthetic events. Thus, based on storage 2200, synthetic event 2202 can be generated by combining and/or analyzing synthetic event 2204 and synthetic event 2206. The resulting synthetic event 2202 is reported and then stored for future analysis.

Figure 23:
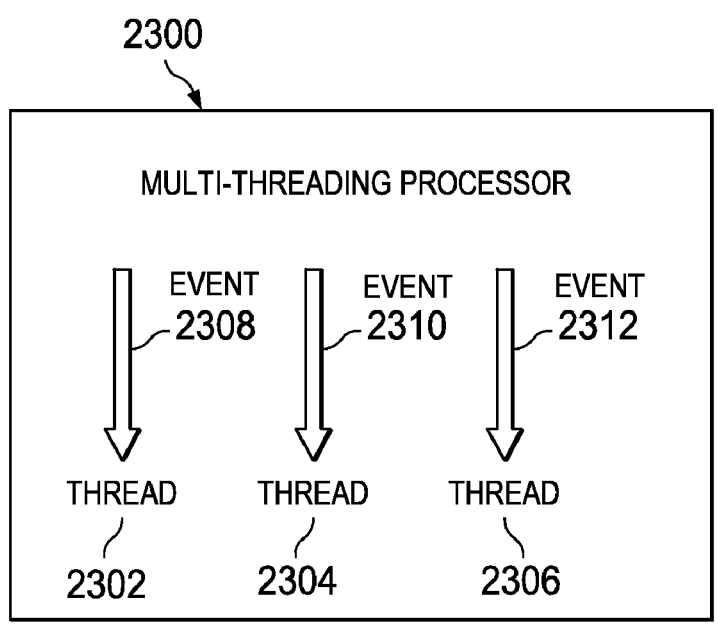
FIG. 23 is a block diagram illustrating processing of events in a processor having multi-threading processing capability, in accordance with an illustrative embodiment.

FIG. 23 is a block diagram illustrating processing of events in a processor having multi-threading processing capability, in accordance with an illustrative embodiment. Processor 2300 can be processor 200 shown in FIG. 2, or can be one or more processors acting together to provide multi-threading functionality. Multi-threading functionality is often provided by parallel-processing processors.

Processor 2300 can be used to more quickly perform synthetic event analysis, as described with respect to FIG. 21. Specifically, each thread, thread 2302, thread 2304, and thread 2306 processes a corresponding distinct event. Thus, thread 2302 processes event 2308, thread 2304 processes event 2310, and thread 2306 processes event 2312. Because each event is processed by a different thread, the entire process of performing analysis is increased. Further, as events or cohorts are combined into broader events or cohorts, the number of threads operating can be decreased. Still further, two or more threads could process different aspects of a single event, thereby further increasing the speed of processing.

FIG. 24 is a flowchart of a process for generating synthetic events, in accordance with an illustrative embodiment. The process shown in FIG. 24 represents a process performed to calculate a synthetic event, such as the synthetic events shown in FIGS. 21 and 22. The process shown in FIG. 24 can be implemented using dynamic analytical framework 1500 in FIG. 15, dynamic analytical framework 1600 in FIG. 16, and possibly include the use of inference engine 1000 shown in FIG. 10. Thus, the process shown in FIG. 20 can be implemented using one or more data processing systems, including but not limited to computing grids, server computers, client computers, network data processing system 100 in FIG. 1, and one or more data processing systems, such as data processing system 200 shown in FIG. 2, and other devices as described with respect to FIG. 1 through FIG. 16. Together, devices and software for implementing the process shown in FIG. 20 can be referred-to as a "system."

The process begins as the system organizes data into cohorts (step 2400). The system then performs inference analysis on the cohorts (step 2402). Inference analysis proceeds according to the techniques particularly described with respect to FIG. 21 and with respect to FIG. 10 through FIG. 20. The system then stores the inferences as synthetic events (step 2404).

The system determines whether the process should be iterated (step 2406). The decision to iterate can be made responsive to either user feedback or to a policy or rules-based determination by a computer that further iteration is needed or desired. Examples of cases that require or should be subject to further iteration include, synthetic events that are flawed for one reason or another, synthetic events that do not have a stable probability (i.e., a small change in initial conditions results in a large variation in probability), the addition of new raw data, the addition of some other synthetic event, or many other examples.

If iteration is to be performed, then the process returns to step 2400 and repeats. Otherwise, the system takes the parallel steps of displaying results (step 2408) and determining whether to generate a new hypothesis (step 2410). A determination of a new hypothesis can be either user-initiated or computer-generated based on rules or policies. A new hypothesis can be considered an event or a fact established as the basis of a query.

If a new hypothesis is to be generated, then the process returns to step 2400 and repeats. Otherwise, the process terminates.

FIG. 25 is a flowchart of a process for generating synthetic events, in accordance with an illustrative embodiment. The process shown in FIG. 25 represents a process performed to calculate a synthetic event, such as the synthetic events shown in FIGS. 21 and 22. The process shown in FIG. 25 can be implemented using dynamic analytical framework 1500 in FIG. 15, dynamic analytical framework 1600 in FIG. 16, and possibly include the use of inference engine 1000 shown in FIG. 10. Thus, the process shown in FIG. 20 can be implemented using one or more data processing systems, including but not limited to computing grids, server computers, client computers, network data processing system 100 in FIG. 1, and one or more data processing systems, such as data processing system 200 shown in FIG. 2, and other devices as described with respect to FIG. 1 through FIG. 16. Together, devices and software for implementing the process shown in FIG. 20 can be referred-to as a "system."

The process begins as the system receives first and second sets of data (step 2500). The system organizes the first and second sets of data into first and second cohorts (step 2502). The system finally processes the first and second cohorts to generate a synthetic event defined by $S(p1) \Longrightarrow F(p2)$, wherein S is a set of inputs including the first and second cohorts, p1 is the probability of the inputs, F is an inferred event, and p2 is a probability of the inferred event (step 2504). The process terminates thereafter.

Thus, the illustrative embodiments provide for a computer implemented method, data processing system, and computer program product for generating synthetic events based on a vast amount of data are provided. A first set of data is received. A second set of data different than the first set of data is received. The first set of data is organized into a first cohort.

The second set of data is organized into a second cohort. The first cohort and the second cohort are processed to generate a synthetic event. The synthetic event comprises a third set of data representing a result of a mathematical computation defined by the operation $S(p1) \Longrightarrow F(p2)$, wherein S comprises a set of input facts with probability p1, wherein the set of input facts comprise the first cohort and the second cohort, and wherein F comprises an inferred event with probability p2. The term "event" means a particular set of data that represents, encodes, or records at least one of a thing or happening. Each of the first set of data, the second set of data, the first cohort, the second cohort, the synthetic event, and subcomponents thereof all comprise different events. The synthetic event is stored.

In another illustrative embodiment, each corresponding event of the different events is represented as a corresponding pointer. Each corresponding subcomponent of an event is represented as an additional corresponding pointer.

In another illustrative embodiment, performing inference analysis includes performing calculations regarding the first cohort using a first thread executing on a processor having multi-threading functionality and performing calculations regarding the second cohort using a second thread executing on the processor. In still another illustrative embodiment, the first cohort comprises a plurality of data and the second cohort comprises a single datum.

In another illustrative embodiment, the first cohort is derived from a first set of sub-cohorts and wherein the second cohort is derived from a second set of sub-cohorts. In yet another illustrative embodiment, directly comparing the first set of data to the second set of data results in computationally explosive processing. In this illustrative embodiment, the first set of data can represent corresponding gene patterns of corresponding patients in a set of humans, and the second set of data can represent gene patterns of a second set of humans.

The illustrative embodiments can include receiving a third set of data, organizing the third set of data into a third cohort, organizing the synthetic event into a fourth cohort, and processing the first cohort, the second cohort, the third cohort, and the fourth cohort to generate a second synthetic event. The second synthetic event is stored.

This illustrative embodiment can also include processing the first synthetic event and the second synthetic event to generate a third synthetic event. The third synthetic event can also be stored.

In another illustrative embodiment, the first set of data represents gene patterns of individual patients, the second set of data represents diet patterns of a population of individuals in a geographical location, the third set of data represents health records of the individual patients, and the synthetic event represents a probability of that a sub-population of particular ethnic origin will develop cancer. The second synthetic event comprises a probability that the individual patients will develop cancer.

In this particular illustrative embodiment, processing the first synthetic event and the second synthetic event generate a third synthetic event, which can be stored. The third synthetic event can comprise a probability that a specific patient in the individual patients will develop cancer.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A computer implemented method comprising:
   receiving a first set of data;
   receiving a second set of data different than the first set of data, wherein directly comparing the first set of data to the second set of data would be computationally explosive;
   organizing the first set of data into a first cohort;
   organizing the second set of data into a second cohort;
   processing the first cohort and the second cohort to generate a first synthetic event, wherein the first synthetic event comprises a third set of data representing a result of a mathematical computation defined by the operation $S(p1) \Longrightarrow F(p2)$, wherein S comprises a set of input facts with probability p1, wherein the set of input facts comprise the first cohort and the second cohort, wherein F comprises an inferred event with probability p2, wherein the term "event" means a particular set of data that represents, encodes, or records at least one of a thing or happening, and wherein each of the first set of data, the second set of data, the first cohort, the second cohort, and the first synthetic event all comprise different events;

receiving a third set of data;
organizing the third set of data into a third cohort;
organizing the synthetic event into a fourth cohort;
processing the first cohort, the second cohort, the third cohort, and the fourth cohort to generate a second synthetic event;
processing the first synthetic event and the second synthetic event to generate a third synthetic event; and
storing the first synthetic event, the second synthetic event, and the third synthetic event.

2. The computer implemented method of claim 1 wherein each corresponding event of the different events is represented as a corresponding pointer.

3. The computer implemented method of claim 2 wherein performing inference analysis comprises:
   performing calculations regarding the first cohort using a first thread executing on a processor having multi-threading functionality; and
   performing calculations regarding the second cohort using a second thread executing on the processor.

4. The computer implemented method of claim 1 wherein the first cohort comprises a plurality of data and the second cohort comprises a single datum.

5. The computer implemented method of claim 1 wherein the first cohort is derived from a first set of sub-cohorts and wherein the second cohort is derived from a second set of sub-cohorts.

6. The computer implemented method of claim 1 wherein the first set of data represents corresponding gene patterns of corresponding patients in a first set of humans, and wherein the second set of data represents gene patterns of a second set of humans.

7. The computer implemented method of claim 1 wherein the first set of data represents gene patterns of individual patients, the second set of data represents diet patterns of a population of individuals in a geographical location, the third set of data represents health records of the individual patients, the synthetic event represents a probability of that a subpopulation of particular ethnic origin will develop cancer, and wherein the second synthetic event comprises a probability that the individual patients will develop cancer.

8. The computer implemented method of claim 7 further comprising:
   processing the first synthetic event and the second synthetic event to generate a third synthetic event; and
   storing the third synthetic event.

9. The computer implemented method of claim 8 wherein the third synthetic event comprises a probability that a specific patient in the individual patients will develop cancer.

10. A computer program product comprising:
   a computer readable medium storing instructions for carrying out a computer implemented method, the instructions comprising:
   instructions for receiving a first set of data;
   instructions for receiving a second set of data different than the first set of data, wherein a direct comparison of the first set of data to the second set of data is computationally explosive;
   instructions for organizing the first set of data into a first cohort;
   instructions for organizing the second set of data into a second cohort;
   instructions for processing the first cohort and the second cohort to generate a first synthetic event, wherein the first synthetic event comprises a third set of data representing a result of a mathematical computation defined by the operation $S(p1) \Longrightarrow F(p2)$, wherein S comprises a set of input facts with probability p1, wherein the set of input facts comprise the first cohort and the second cohort, wherein F comprises an inferred event with probability p2, wherein the term "event" means a particular set of data that represents, encodes, or records at least one of a thing or happening, and wherein each of the first set of data, the second set of data, the first cohort, the second cohort, and the first synthetic event all comprise different events;
   instructions for receiving a third set of data;
   instructions for organizing the third set of data into a third cohort;
   instructions for organizing the synthetic event into a fourth cohort;
   instructions for processing the first cohort, the second cohort, the third cohort, and the fourth cohort to generate a second synthetic event;
   instructions for processing the first synthetic event and the second synthetic event to generate a third synthetic event; and
   instructions for storing the first synthetic event, the second synthetic event, and the third synthetic event.

11. The computer program product of claim 10 wherein each corresponding event of the different events is represented as a corresponding pointer.

12. The computer program product of claim 11 wherein the instructions for performing inference analysis comprises:
   instructions for performing calculations regarding the first cohort using a first thread executing on a processor having multi-threading functionality; and
   instructions for performing calculations regarding the second cohort using a second thread executing on the processor.

13. A data processing system comprising:
   a bus;
   a processor connected to the bus, the processor having multi-threaded functionality;
   a memory connected to the bus, the memory storing instructions for carrying out a computer implemented method, wherein the processor is capable of carrying out the instructions to:
   receive a first set of data;
   receive a second set of data different than the first set of data, wherein a direct comparison of the first set of data to the second set of data is computationally explosive;
   organize the first set of data into a first cohort;
   organize the second set of data into a second cohort; and
   process the first cohort and the second cohort to generate a first synthetic event, wherein the first synthetic event comprises a third set of data representing a result of a mathematical computation defined by the operation $S(p1) \Longrightarrow F(p2)$, wherein S comprises a set of input facts with probability p1, wherein the set of input facts comprise the first cohort and the second cohort, wherein F comprises an inferred event with probability p2, wherein the term "event" means a particular set of data that represents, encodes, or records at least one of a thing or happening, and wherein each of the first set of data, the second set of data, the first cohort, the second cohort, and the first synthetic event all comprise different events
   receive a third set of data;
   organize the third set of data into a third cohort;
   organize the synthetic event into a fourth cohort;
   process the first cohort, the second cohort, the third cohort, and the fourth cohort to generate a second synthetic event;

process the first synthetic event and the second synthetic event to generate a third synthetic event; and store the first synthetic event, the second synthetic event, and the third synthetic event.

14. The data processing system of claim 13 wherein each corresponding event of the different events is represented as a corresponding pointer.

15. The data processing system of claim 14 wherein the processor is further capable of executing the instructions to:
perform calculations regarding the first cohort using a first thread executing on the processor; and
perform calculations regarding the second cohort using a second thread executing on the processor.

* * * * *